US006126922A

United States Patent [19]
Rozzi et al.

[11] Patent Number: 6,126,922
[45] Date of Patent: *Oct. 3, 2000

[54] FLUORID-RELEASING COMPOSITIONS AND COMPOSITIONS WITH IMPROVED RHEOLOGY

[75] Inventors: Sharon M. Rozzi, Stillwater; Sumita B. Mitra, West St. Paul; Bing Wang, Woodbury, all of Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/835,975

[22] Filed: Apr. 11, 1997

Related U.S. Application Data

[63] Continuation-in-part of application No. 08/560,332, Nov. 17, 1995, abandoned.

[51] Int. Cl.[7] .................... A61K 7/16; A61K 7/20
[52] U.S. Cl. .................. 424/49; 424/52; 424/53; 424/56; 523/116
[58] Field of Search .................. 523/116; 424/49, 424/52, 53, 56

[56] References Cited

U.S. PATENT DOCUMENTS

| | | | |
|---|---|---|---|
| 5,063,257 | 11/1991 | Akahane et al. | 523/116 |
| 5,300,283 | 4/1994 | Prencipe et al. | 424/49 |
| 5,922,786 | 7/1999 | Mitra et al. | 523/116 |
| 5,955,514 | 9/1999 | Huang et al. | 523/116 |

FOREIGN PATENT DOCUMENTS

| | | |
|---|---|---|
| 56-120610 | 2/1981 | Japan . |
| 97/18792 | 5/1997 | WIPO . |

OTHER PUBLICATIONS

Abstract JP 56120610A Sep. 22, 1981.

*Primary Examiner*—Thurman K. Page

[57] ABSTRACT

Dental compositions are provided comprising a) a polymerizable component, b) a fluoride-releasing material, c) a hydrophilic component, d) a polymerization initiator, and e) an acidic component. This dental composition is substantially free of added water, and has a Water Uptake Value of at least about 1.5 g of water per 100 g composition in 2 weeks. Compositions are also provided that comprise a) a polymerizable component, b) acid reactive filler, c) a hydrophilic component, d) a polymerization initiator, and e) an acidic component. The above materials are provided in amounts sufficient that the resulting composition has extremely desirable rheological properties.

47 Claims, No Drawings

FLUORID-RELEASING COMPOSITIONS AND COMPOSITIONS WITH IMPROVED RHEOLOGY

This application is a continuation-in-part of U.S. Ser. No. 08/560,332, filed Nov. 17, 1995 and now abandoned.

FIELD OF THE INVENTION

This invention relates to a novel dental composition or article that is hydrophilic and is compatible in the humid oral environment. In another aspect, the composition and article allow for the release of fluoride ions at a high level and in a sustained manner. The compositions of the invention are generally intended for placement followed by in-situ curing, although these compositions are also quite suitable for the fabrication of pre-polymerized articles intended for oral applications.

BACKGROUND

Many types of materials have been developed to restore tooth. Although the use of amalgam has been common in dentistry, over the last few decades the tooth-colored restorative materials have become more popular. These compositions generally comprise polymerizable ethylenically unsaturated monomers and an inert filler. The resin systems generally consist of mixtures of Bis-GMA, TEGDMA, Urethane dimethacrylates etc. The resultant restorative compositions are generally quite hydrophobic and immiscible with water, and hence require the elimination of water from the surface of the tooth structure to be restored. The clinical procedure calls for stringent moisture control through the use of rubber dam or other suitable procedure. However, since moisture is constantly replenished in the mouth through saliva flow and/or exudation of dentinal fluid, its control makes the restorative procedure quite challenging for the practitioner. Hydrophilic compositions, on the other hand, can imbibe water from the surrounding environment. Water-based cement compositions, particularly the glass ionomer cements, are tolerant of extraneous moisture. Thus the cements described by Wilson et al. have been used advantageously. These are two part powder:liquid systems consisting of a solution of a polyalkenoic acid in water and an acid-reactive glass powder. Modifications of these cements by incorporation of curable moieties to obtain in situ polymerizable cements have been described. A particularly attractive benefit of these cements is the prolonged release of high amounts of fluoride from the set cements in the oral environment. It is believed that this leads to a protection from secondary caries attack. The disadvantage of these cements, however, is that they are generally two-part powder:liquid systems and require mixing prior to use. Furthermore, the glass ionomer cement materials in general have much lower mechanical properties compared to the resin-based composites. Hence their use is confined to non-stress bearing applications. In order to overcome this disadvantage, other systems have been devised, such as described in U.S. Pat. No. 5,151,453. The fluoride release levels from these materials, however, is quite low compared to the glass ionomer cements.

Additionally, having good handling properties in restorative filling materials is so important to the dentist, it is not surprising that there are numerous citations in the literature claiming materials with such properties. See e.g. DE 4447275; JP 56120610; JP 03077804; JP 06065022; JP 07061904; JP 08119820; EP 176777; EP 436382; U.S. Pat. No. 3,721,644; U.S. Pat. No. 3,766,132; U.S. Pat. No. 3,770,811; U.S. Pat. No. 4,150,485; U.S. Pat. No. 4,514,174; U.S. Pat. No. 5,318,999; and Lee, H. L., et al (Aust. Dent. J., 22(4), 1977, 232–5). None of these citations, however, describe the specific materials of the present invention nor do they describe the rheology requirements to construct a dental compostion with superior handling capabilities.

SUMMARY OF THE INVENTION

In the present invention, a dental composition is provided comprising a) a polymerizable component, b) a fluoride-releasing material, c) a hydrophilic component, d) a polymerization initiator, and e) an acidic component. This dental composition is substantially free of added water, and has a "Water Uptake Value" of at least about 1.5 g of water per 100 g composition in 2 weeks.

In another aspect of the present invention, a dental composition is provided comprising a) a polymerizable component, b) acid reactive filler, c) a hydrophilic component, d) a polymerization initiator, and e) an acidic component. The above materials are provided in amounts sufficient that the resulting composition has the following rheological properties: 1) the composition has a yield stress between about 3000 and 9000 Pa at 25° C., and between about 2900 and 5000 Pa at 34° C., 2) the composition has a viscosity of between about 100,000 and 500,000 Pa-s at 34° C. and shear rate of 0.001 sec-1, a viscosity of between about 80,000 and 250,000 Pa-s at 34° C. at a shear rate of 0.01 sec-1, and between about 20,000 and 100,000 Pa-s at 34° C. at a shear rate of 0.1 sec-1, and 3) the composition has a tan δ value of between about 0.4 and 1 at 0.10 rad/s and 34° C., a tan δ value between about 1 and 2.5 at 34° C. and 10 rad/sec, a tan δ value between about 1 and 1.7 at 21° C. and 0.10 rad/sec, and a tan δ value between about 1 and 5 at 21° C. and 10 rad/sec.

DETAILED DESCRIPTION OF THE INVENTION

The invention overcomes the disadvantages of low fluoride release of non-aqueous-based dental materials and yet provides cured systems of high mechanical strength.

In another aspect of the present invention, materials are provided having good handling properties. Dentists have been surveyed for their needs concerning dental restorative filling materials, and their response has been that the most important need is for the filling material to have good handling properties. Good handling properties in a filling material translates to time savings in performing a dental restoration. The class of dental restorative filling materials in the present invention do not slump, yet easily adapt to a cavity preparation, and are easily contoured and feathered; they do not stick to placement instruments; and overall they are fast and easy to use to restore tooth structure. The novel dental composition or article is hydrophilic and is compatible in the humid oral environment. The compositions of the invention are generally intended for placement followed by in-situ curing.

"Slump" refers to the phenomenon of flow under the force of gravity It is desirable that dental restorative filling materials do not slump because after they are placed in the mouth and contoured the dentist wants the imparted shape to remain unchanged until the materials are cured. Materials with a sufficiently high yield stress will not slump; that is, they will not flow under the stress of gravity. The yield stress of a material is the minimum stress required to cause the material to flow, and is described in Rheology Principles, Measurements, and Applications, C. W. Macosko, VCH Publishers, Inc., New York, 1994, p. 92. If the stress due to gravity is below the yield stress of the material, then the material will not flow. The stress due to gravity will depend on the mass of restorative filling material being placed and the shape. It is desirable that the yield stress of a dental restorative filling material be sufficiently high that the material does not slump in all types and sizes of cavity preparations. It has been found that the class of dental restorative filling materials having a yield stress between about 3000 and 9000 Pa at 25° C., and between about 2500 and 5000 Pa at 34° C. do not slump at room temperature nor at mouth temperature. Materials having a viscosity at a shear rate of 0.01 $\sec^{-1}$ between about 80,000 and 250,000 Pa-s at 34° C. easily adapt to a cavity preparation.

"Contouring" refers to the process of shaping the restorative filling material with dental instruments so that it resembles the natural dental anatomy. For easy contouring materials should have a sufficiently high viscosity that they maintain their shape after manipulation with a dental instrument, and yet the viscosity should not be so high that it is difficult to shape the material. For easy contouring materials should not stick to placement instruments otherwise when the instrument is removed the shape will be altered. The class of materials having a viscosity at 0.001 $\sec^{-1}$ between about 100,000 and 500,000 Pa-s at 34° C. are not sticky or runny, and are easily contoured.

"Feathering" refers to the process of reducing the restorative filling material to a thin film in order to blend the material into the natural dentition. This is done with a dental instrument at the margin of the restoration and the natural dentition. Surprisingly, materials having a viscosity at a shear rate of 0.1 $\sec^{-1}$ between about 20,000 and 100,000 Pa-s at 34° C. are easily feathered.

Another useful means for characterizing the handling properties of dental restorative filling materials are dynamic rheological measurements. These measurements are useful in quantifying the balance of fluid and solid behavior in viscoelastic materials such as dental restorative filling materials. In these measurements (described in detail in Macosko, page 121) a low amplitude, sinusoidal strain ($\gamma$) is applied to a material and the resultant sinusoidal stress ($\tau$) is measured. The stress wave will be of the same frequency as the applied strain wave, but will generally be shifted by a phase angle $\delta$. For pure solid materials (like steel), the stress and strain waves are in phase and $\delta=0°$. For liquid materials (like water or glycerine), the stress and strain waves are completely out of phase and $\delta=90°$. Materials for which $0<\delta<90°$ are termed viscoelastic meaning that they have both viscous (liquid) and elastic (solid) properties. Materials for which $0<\delta<45°$ are termed viscoelastic solids implying that they are more solid-like than liquid-like. Likewise, materials for which $45<\delta<90°$ are termed viscoelastic liquids implying that they are more liquid-like than solid-like.

The ratio of the stress ($\tau_o$) and strain ($\gamma_o$) amplitudes in a dynamic rheological measurement is the complex modulus G*. G* can be broken down into the contributions from the solid- and liquid-like behaviors in a material by separating the components that are in-phase and out-of-phase with the applied strain, respectively. The elastic modulus G' is the component of G* that is in-phase with the applied strain and is equal to G* cos $\delta$. The viscous modulus G" is the component of G* that is out-of-phase with the applied strain and is equal to G* sin $\delta$. The ratio of the viscous to the elastic modulus, G"/G' is tan $\delta$ and is a measure of the balance of solid- and liquid-like properties in a material. Materials for which tan $\delta<1$ are viscoelastic solids. Materials for which tan $\delta>1$ are viscoelastic liquids.

In these dynamic rheological measurements it is important that the strains used are sufficiently small so that the structure of a material is being probed and not broken. Strains are sufficiently small if the choice of the strain does not effect the value of G*, G', and G". When this is true, the measurements are made in the "linear viscoelastic region" of a material.

There is an association between the frequency in a dynamic rheological measurement and the shear rate in a steady shear measurement. This means when characterizing how a material will behave in a low shear rate process (like slump and contouring), low frequencies should be used in dynamic rheological measurements. Likewise, when characterizing how a material will behave in a high shear rate process (like filling a cavity preparation and feathering), high frequencies should be used in dynamic rheological measurements.

Unexpectedly, we have found that specific ranges of tan $\delta$ provide exceptional handling characteristics. The class of dental restorative filling materials in the present invention are viscoelastic solids when perturbed at mouth temperature and at low frequency; that is, at 0.10 rad/s and 34° C. the ratio of the viscous modulus (G") to the elastic modulus (G'), or tan $\delta$, is between about 0.4 and 1. It has been found that materials that have tan $\delta$ between about 0.4 and 1.0 at 0.10 rad/s and 34° C. are easy to contour and do not slump. At mouth temperature and at high frequency, 34° C. and 10 rad/sec, these materials have a tan $\delta$ value between about 1 and 2.5 Materials that have a tan $\delta$ value between about 1 and 2.5 at 34° C. and 10 rad/sec are easily adapted to a cavity preparation and are easy to feather. Surprisingly, it has been found that for ease of transferring the composite from ambient conditions to the oral environment, it is preferred that these composites additionally have a tan $\delta$ value between about 1 and 1.7 at room temperature about (21° C.) and at 0.10 rad/sec, and have a tan $\delta$ value between about 1 and 5 at 10 rad/sec and room temperature.

For purposes of the present invention, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect of the long term properties of the composition. For example, water should not be present in an amount that would facilitate reaction of the acid-reactive filler with the acidic component so that lumpiness or graininess of the material develops during commercially required storage time.

The polymerizable component of the present compositions are compounds, which may be monomers, oligomers, or polymers, containing a polymerizable group. These polymerizable groups may be selected from free radically polymerizable groups, cationically polymerizable groups, or mixtures thereof. Preferably, the polymerizable compound has a molecular weight of between about 100 to 5000, and more preferably, has a molecular weight between about 300 and 1000. Mixtures of both higher and lower molecular weight polymerizable materials are also contemplated as providing special benefits in handling properties and the physical properties of the ultimate cured material. In a preferred aspect of the present invention, at least some of the polymerizable material is relatively lower in viscosity than other ingredients of the composition so that it serves a viscosity lowering function in the overall uncured material. Preferably, at least some of the polymerizable material has a viscosity of less than about 2 Pa-s, more preferably less than about 0.5 Pa-s, and most preferably less than about 0.3 Pa-s. Blends of materials exhibiting such viscosity characteristics are desireable as well.

Preferred materials that provide the polymerizable component are the esters of acrylic or methacrylic acid. Examples of these compounds are methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("Bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate [where the number of repeating ethylene oxide units vary from 2 to 30, especially triethylene glycol dimethacrylate ("TEGDMA")], neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl- 2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis [3(4-phenoxy)-2-hydroxypropane-1-methacrylate]propane, 2,2'-bis[3(4-phenoxy)-2-hydroxypropane-1-acrylate]propane, and the like.

Other preferred polymerizable components can be substituted acryl amides and methacrylamides. Examples are acrylamide, methylene bis-acrylamide, methylene bis-methacrylamide, diacetone/acrylamide diacetone methacylamide, N-alkyl acrylamides and N-alkyl methacrylamides where alkyl is a lower hydrocarbyl unit of 1–6 carbon atoms. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Alternatively, the polymerizable component may be a cationically cured material, such as epoxy materials, oxetanes, oxolanes, cyclic acetals, lactams, lactones, and vinyl ethers or spirocyclic compounds containing O atoms in the rings.

The cationically polymerizable epoxy resins useful in the compositions of the invention comprise organic compounds having an oxirane ring, i.e.,

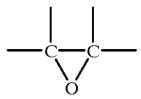

polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, and preferably at least about 1.5 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures containing one, two, or more epoxy groups per molecule. The "average" number of epoxy groups per molecule is determined by dividing the total number of epoxy groups in epoxy-containing material by the total number of epoxy molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as the epoxycyclohexanecarboxylates, typified by 3,4- epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, incorporated herein by reference.

Further epoxy-containing materials which are particularly useful in the practice of this invention include glycidyl ether monomers of the formula

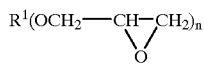

where $R^1$ is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.). bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-metadioxane (e.g., "ERL-4234" from Union Carbide Corp.), vinylcyclohexene monoxide (from Union Carbide Corp.), 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g.,"HELOXY Modifier 62" from Shell Chemical Co.), p-tert butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, e.g., epichlorohydrin; alkylene oxides, e.g., propylene oxide, styrene oxide; alkenyl oxides, e.g., butadiene oxide; glycidyl esters, e.g., ethyl glycidate.

The polymers of the epoxy resin may optionally contain other functionalities that do not substantially interfere with cationic cure at room temperature.

Blends of various epoxy-containing materials are particularly contemplated in this invention. Examples of such blends include two or more molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical nature, such as aliphatic and aromatic, or functionality, such as polar and non-polar. Other cationically polymerizable polymers may additionally be incorporated. Particularly preferred epoxy containing compositions also contain materials having hydroxyl functionality.

Mixtures of polymerizable materials, including hybrid systems containing both free-radically polymerized components and cationically polymerized components, are also contemplated.

The fluoride-releasing material of the present invention may be naturally occuring or synthetic fluoride minerals, fluoride glass such as fluoroaluminosilicate glass, simple and complex inorganic fluoride salts, simple and complex organic fluoride salts or combinations thereof. Optionally these fluoride sources can be treated with surface treatment agents.

Examples of the fluoride-releasing material are fluoroaluminosilicate glasses described in U.S. Pat. No 3,814,717, which may be optionally treated as described in U.S. Pat. No. 5,332,429, the disclosures of which are both incorporated by reference herein.

The fluoride releasing material may optionally be a metal complex described by formula

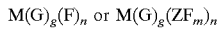

where M represents an element capable of forming a cationic species and having a valency of 2 or more, G is an organic chelating moiety capable of complexing with the element M Z is hydrogen, boron, nitrogen, phosphorus, sulfur, antimony, arsenic F is a fluoride atom g, m and n are at least 1.

Examples of preferred M elements are the metals of groups IIA, IIIA, IVA, and transition and inner transition metal elements of the periodic table. Specific examples include $Ca^{+2}$, $Mg^{+2}$, $Sr^{+2}$, $Zn^{+2}$, $Al^{+3}$, $Zr^{+4}$, $Sn^{+2}$, $Yb^{+3}$, $Y^{+3}$, $Sn^{+4}$. Most preferably, M is $Zn^{+2}$.

The G group, as noted above, is an organic chelating moiety. This chelating moiety may or may not contain a polymerizable group. Although not absolutely essential, in some instances it may be advantageous for the chelating moiety to contain a polymerizable functionality that matches the reactivity of the polymerizable matrix into which it is incorporated.

A wide range of chelating moieties may be used in the present invention. Chelates in which the metal ion is bound in a ring structure of 4–8 members are preferred, with the 5–7 membered ring chelates being particularly preferred. The chelates useful in the present invention are multidentate, and are preferably bi-, tri- or quadra-dentate. Chelates containing hydroxyl or carboxy groups or both are more particularly preferred. Examples of such chelating agents are tartaric acid, citric acid, ethylenediamine tetraacetic acid, salicylic acid, hydroxybenzoic acids, hydroxytartaric acids, nitrilotriacetic acid, salicylic acid, melletic acids, and polyglycols. Chelates containing one or more acid groups derived from phosphorus, boron or sulfur can also be used, with the proviso that the molecular weight of the chelating agent is less than about 1000. Examples of especially suitable metal chelates include complexes of β-diketones and β-ketoesters.

The polymerizable metal-fluoride chelates preferably contain one or more polymerizable groups that match the reactivity of the polymerizable matrix into which it is incorporated. In addition to the chelating functionalities outlined above, these complexes can contain ethylenically unsaturated groups, epoxy groups, ethyleneimine groups and the like.

Preferred G groups include the polyphosphates, such as sodium tripolyphosphate and hexametaphosphoric acid; aminocarboxylic acids, such as ethylenediaminetetraacetic acid, hydroxyethylethylenediaminetriacetic acid, nitrilotriacetic acid, N-dihydroxyethylglycine and ethylenebis (hydroxyphenylglycine); 1,3-diketones, such as acetylacetone, trifluoroacetylacetone and thenoyltrifluoroacetone; hydroxycarboxylic acids, such as malic acid, tartaric acid, citric acid, gluconic acid, and 5-sulfosalicylic acid; polyamines, such as ethylenediamine, triethylenetetramine and triaminotriethylamine; aminoalcohols, such as triethanolamine and N-hydroxyethylethylenediamine; aromatic heterocyclic bases, such as dipyridyl and o-phenanthroline; phenols, such as salicyladehyde, disulfopyrocatechol and chromotropic acid; aminophenols, such as oxine, 8-hydroxyquinoline and oxinesulfonic acid; oximes, such as dimethylglyoxime and salicyladoxime hydroxamic acid and its derivative; Schiff bases, such as disalicyladehyde 1,2-propylenedimine; tetrapyrroles, such as tetraphenylporphin and phthalocyanine; sulfur compounds, such as toluenedithiol(Dithiol), dimercaptopropanol, thioglycolic acid, potassium ethylxanthate, sodium diethyldithiocarbamate, dithizone, diethyl dithiophosphoric acid and thiourea; synthetic macrocyclic compounds, such as dibenzo[18]crown-6(5), $(CH_3)_6[14]4,11$-diene$N_4(6)$ and (2.2.2-cryptate) (7); polymeric compounds such as polyethylenimine, polymetharyloylacetone, and poly(p-vinylbenzyliminodiacetic acid); and phosphonic acids, such as nitrilotrimethylenephosphonic acid, ethylenediaminetetra (methylenephosphonic acid) and hydroxyethylidenediphosphonic acid.

Particularly preferred G groups are compounds of the following formulas:

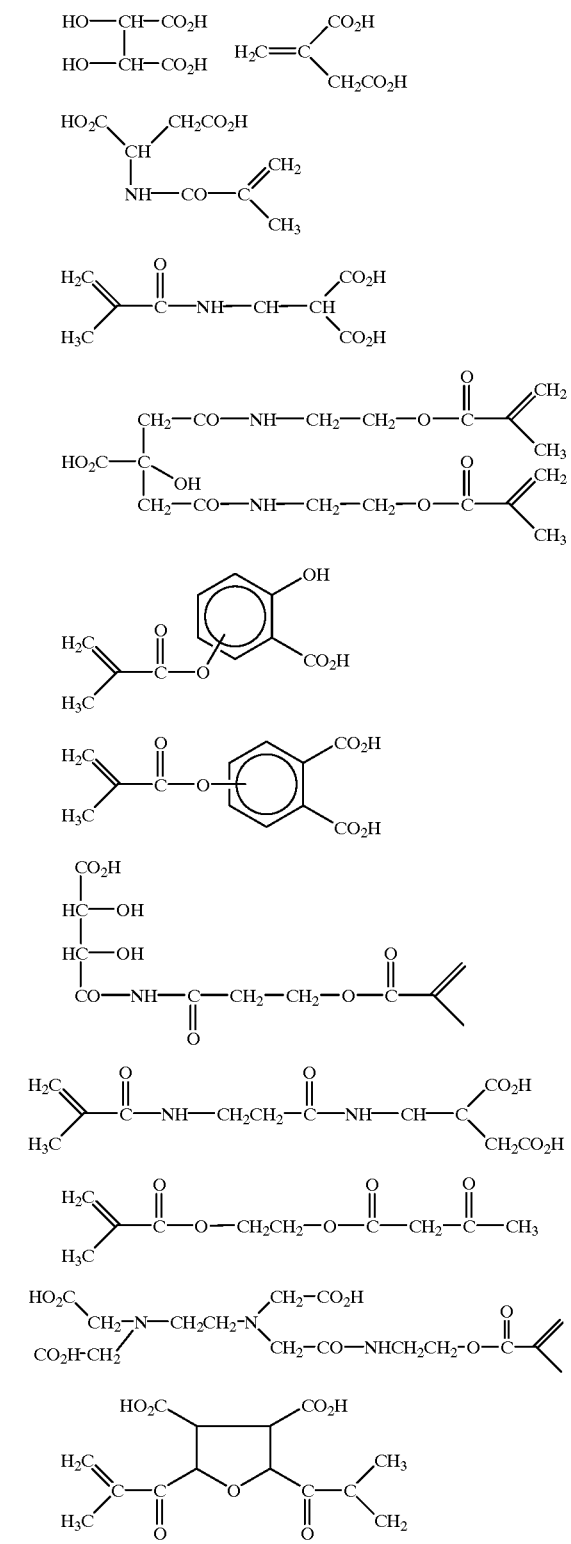

-continued

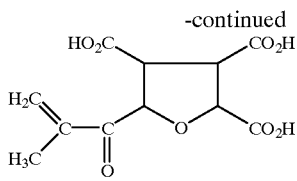

Fluoride is associated with the complexed metal as either a counterion or as a ligand. Thus, the designation (YF) above indicates that the fluoride is associated with the Y group as a complex, which in turn is associated with the metal as a counterion or as a ligand.

Particularly preferred compositions of the present invention comprise at least two sources of fluoride. The first source is the fluoride-containing metal complex as described above. The second source is a fluoride-releasing fluoroaluminosilicate glass. With the use of both materials, excellent fluoride release is provided both in the initial period and over the long term use of the composition.

The hydrophilic component can be provided as a monomer, oligomer or polymer. Preferably, it is provided as either a linear homopolymer or copolymer, either of which may optionally be lightly crosslinked. The hydrophilic component is preferably miscible in water at concentrations of about 3% by weight or can absorb at least 2 g of water per hundred g of polymer. Optionally, the hydrophilic component can be a hydrophilic monomer which undergoes polymerization in situ leading to a hydrophilic, water-absorbing polymer. A hydrophilic component with a molecular weight between about 5,000 and 500,000 is preferred. Most preferred is a hydrophilic component with a molecular weight between about 5,000 and 100,000.

In many cases, compounds containing acidic functionality are hydrophilic in nature. Such compounds may be useful in the present invention if they satisfy the above hydrophilicity characteristics. It has been found, however, that preferred hydrophilic components for use in the present invention have at least a portion of their hydrophilic properties provided by non-acidic functionalities. Thus, preferred hydrophilic compounds for use in the present invention contain acidic functionality and non-acidic hydrophilic functionality, and most preferred hydrophilic compounds for use in the present invention contain no acidic functionalities.

Examples of hydrophilic components include monomers or polymers such as pyrrolidone, a moiety containing hydroxy groups and polyether groups, a moiety containing a sulfonate group ($SO_3$), a moiety containing a sulfonic group ($SO_2$), N-oxysuccinimide, N-vinylacetamide and acrylamide.

More specific examples of preferred hydrophilic components are non-ionic polymers or copolymers, e.g. polyalkylene oxides (polyoxymethylene, polyethyleneoxide, polypropylene oxide) polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphosphoric and phosphonic acids in unionized, partially neutralized or fully neutralized form.

Generally, any compound having a polar group may provide a hydrophilic aspect to a composition. Preferred hydrophilic compounds may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups. More specific examples of such groups follow.

The hydrophilic component may be derived from mono- or multifunctional carboxyl group containing molecules represented by the general formula:

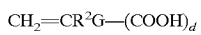

where $R^2$=H, methyl, ethyl, cyano, carboxy or carboxymethyl, d=1–5 and G is a bond or a hydrocarbyl radical linking group containing from 1–12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid and N-acryloyl glycine.

The hydrophilic component may, for example, be derived from mono- or multifunctional hydroxy group containing molecules represented by the general formula:

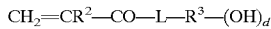

where $R^2$=H, methyl, ethyl, cyano, carboxy or carboxyalkyl, L=O, NH, d=1–5 and $R^3$ is a hydrocarbyl radical of valence d+1 containing from 1–12 carbon atoms. The preferred monomers in this class are hydroxyethyl (meth)acrylate, hydroxypropyl (meth)acrylate, hydroxybutyl (meth) acrylate, glycerol mono(meth)acrylate, tris(hydroxymethyl) ethane monoacrylate, pentaerythritol mono(meth)acrylate, N-hydroxymethyl (meth)acrylamide, hydroxyethyl (meth) acrylamide and hydroxypropyl (meth)acrylamide.

The hydrophilic component may alternatively be derived from mono- or multifunctional amino group containing molecules of the general formula:

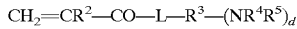

where $R^2$, L, $R^3$, and d are as defined above and $R^4$ and $R^5$ are H or alkyl groups of 1–12 carbon atoms or together they constitute a carbocyclic or heterocyclic group. Preferred monomers of this class are aminoethyl (meth)acrylate, aminopropyl (meth)acrylate, N,N-dimethylaminoethyl (meth) acrylate, N,N-diethylaminoethyl (meth)acrylate, N,N-dimethylaminopropyl (meth)acrylamide, N-isopropylaminopropyl (meth)acrylamide and 4-methyl-1-acryloyl-piperazine.

The hydrophilic component may also be derived from alkoxy substituted (meth)acrylates or (meth)acrylamides such as methoxyethyl (meth)acrylate, 2(2-ethoxyethoxy) ethyl (meth)acrylate, polyethylene glycol mono(meth) acrylate or polypropylene glycol mono(meth)acrylate.

Hydrophilic components may be derived from substituted or unsubstituted ammonium monomers of the general formula:

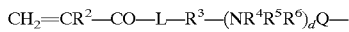

where $R^2$, $R^3$, $R^4$, $R^5$, L and d are as defined above, and where $R^6$ is H or alkyl of 1–12 carbon atoms and Q— is an organic or inorganic anion. Preferred examples of such monomers are 2-N,N,N-trimethylammonium ethyl (meth) acrylate, 2-N,N,N-triethylammonium ethyl (meth)acrylate, 3-N,N,N-trimethylammonium propyl (meth)acrylate, N(2-N',N',N'-trimethylammonium) ethyl (meth)acrylamide, N-(dimethyl hydroxyethyl ammonium) propyl (meth) acrylamide etc. where the counterion may be fluoride, chloride, bromide, acetate, propionate, laurate, palmitate, stearate etc. The monomer can also be N,N-dimethyl diallyl ammonium salt of an organic or inorganic counterion.

Ammonium group containing polymers can also be prepared by using as the hydrophilic component any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The hydrophilic component of the invention can also be derived from sulfonic acid group containing monomers, such as vinyl sulfonic acid, styrene sulfonic acid, 2-acrylamido-2-methyl propane sulfonic acid, allyloxybenzene sulfonic acid, and the like. Alternatively, the hydrophilic component may be derived from phosphorous acid or boron acid group-containing monomers. These monomers may be used in the protonated acid form as monomers and the corresponding polymers obtained may be neutralized with an organic or inorganic base to give the salt form of the polymers.

Compositions of the invention contain one or more suitable polymerization initiators, so that the composition may be polymerized in use. The initiator is selected such that it is capable of initiating the polymerization of the polymerizable material. That is, if the polymerizable material is a free radical polymerizable material, the initiator is a free-radical polymerization initiator. Likewise, if the polymerizable material is a cationically polymerizable material, the initiator is a cationic polymerization initiator.

Compositions of the invention that are free-radically polymerized preferably contain one or more suitable photopolymerization initiators that act as a source of free radicals when activated. Such initiators can be used alone or in combination with one or more accelerators and/or sensitizers.

The photoinitator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The compositions of the present invention may alternatively incorporate a mode of initiation of the polymerization reaction to initiate a crosslinking reaction without the need to expose the system to visible light. A preferred alternative mode for initiation of the polymerization reaction is the incorporation of an oxidizing agent and a reducing agent as a redox catalyst system to enable the dental composition to cure via a redox reaction. Various redox systems is described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include amines (and preferably aromatic amines), ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

When redox initiator systems are used to photoinitiator systems, because care must be taken to keep the reducing agent from reacting with the oxidizing agent before polymerization is desired. Generally, the use of a redox system necessitates providing the material in a two-part format. One-part dental compositions utilizing a photoinitiator system are preferred.

For compositions that are polymerized by a cationic mechanism, suitable initiators include salts that are capable of generating cations such as the diaryliodonium, triarylsulfonium and aryldiazonium salts. Use of electronic donors or peroxides in such systems are also useful for enhancing rate of cure and depth of cure. Simultaneous photoinitiation of cationic and free radical groups may be afforded by, for example, onium salts or organometallic compounds in combination with or wtihout oxidizing agents. Organometallic compounds can be selected from compounds that undergo sigma bond cleavage upon photolysis. The sigma bond is usually a metal-metal bond. Examples of suitable organometallic compounds include [Co Fe(CO)$_2$]$_2$, Mn(CO)$_{10}$, and Mn$_2$(CO)$_{10}$, in combination with iodonium salts and peroxides.

The acidic component of the compositions of the present invention is provided by compounds that are monomers, oligomers or polymers of molecular weight less than about 10,000 and containing at least one acidic group. The acidic group is preferably selected from oxyacids or thio-oxy acids of B, C, N, S, P. More preferably, the acidic component is a compound that is an acid of C or P. If desired, a precursor to the acid such as an acid anhydride, e.g., 4-Methacryloxyethyl Trimellitate Anhydride (4-META), or ester can be used in place of the acid itself, e.g., to generate the desired acid in situ. Suitable acids include, carboxylic acids, sulfonic acids, and phenols, with carboxylic acids, alkylsulfonic acids, arylsulfonic acids, and phosphonic acids being preferred.

Suitable organic acids include acetic acid, α-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-Hema ester of 1,2,4,5 benzenetetracarboxylic acid, 2,4-dinitrophenol, formic acid, fumaric acid, 2-hydroxy-4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters (such as 2,2'-bis(a-methacryloxy-b-hydroxypropoxyphenyl) propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired. Preferred acids are capable of complexing with a reactive glass.

The mixtures can if necessary also contain other compounds that although they contain acid groups, their salts, or their reactive derivative groups, do not contain polymerizable groups. Preferred in this case are multibasic acids such as tartaric, citric, mellitic, polycarboxylic, polyphosphoric, polyphosphonic, or polysulfonic acids along with chelating agents such as ethylenediamine-tetraacetic acid, and especially their salts.

Particularly preferred compositions of the present invention are those wherein at least a portion of the polymerizable component and at least a portion of the acidic component of the composition are provided by the same chemical compound. Examples of such compounds are monomers, oligomers or polymers of molecular weight less than about 50,000 and containing at least one acidic groups and at least one polymerizable group. Preferably, these compounds have a molecular weight of between about 300–5000, and more preferably between about 300–1000. The acidic group can be oxyacids or thio-oxy acids of B, C, N, S, P. Preferably it is an acid of C or P.

These preferred compounds are defined by the structure (P)$_p$—(Q)$_q$—(R)$_r$—
where P=backbone with acidic functionality
  Q=backbone with a curable group, e.g. acrylate, methacrylate, epoxy etc
  R=backbone of a non-reactive modifying unit
  p≧1, q>1, and r=0 or more.

Especially preferable acid groups are carboxylic acids, sulfonic acids, phoshoric acids, phosphonic acids, and boric acids, the salts of the foregoing acids or precursors of the foregoing acids that are easily converted to these acids in conditions encountered during a dental restorative procedure. Examples of such compounds are acryloyl or methacryloyl substituted polycarboxylic acids, phosphoric acid esters of hydroxyethyl methacrylate, hydroxy propyl methacrylate, acrylates and methacrylates of pentaerythritol dimethacrylate dipentaerythritol penta-acrylate and glyceroldimethacrylate.

Examples of such preferred compounds include the aliphatic carboxy compounds, such as acrylic acid, methacrylic acid, maleic acid, fumaric acid, itaconic acid, crotonic acid, aconitic acid, glutaconic acid, mesaconic, citraconic acid, acid, tiglicinic acid, 2-chloroacrylic acid, 3-chloroacrylic acid, 2-bromoacrylic acid, 1-methacryloyl malonic acid, 1-acryloyl malic acid, N-methacryloyl and N-acryloyl derivatives of amino acids, and acids such as tartaric acid, citric acid, malic acid that have been further functionalized with an ethylenic functionality. For example, citric acid may be ethylenically functionalized by substituting with an acryloyl or methacryloyl functionality. These polymerizable groups may be attached directly to the acid containing compound, or may be optionally attached through a linking group. Preferred linking groups include substituted or unsubstituted alkyl, alkoxyalkyl, aryl, aryloxyalkyl, alkoxyaryl, aralkyl or alkaryl groups. Particularly preferred linking groups comprise an ester functionality and most particularly preferred linking groups comprise an amide functionality.

Other preferred compounds are the aromatic carboxy compounds, such as benzoic acid, and acryloyl or methacryloyl derivatives of salicyclic acid, trimellitic acid, phthalic acid, and the like.

Reactive fillers may be included compositions of the present invention, which may or may not have the property of releasing fluoride. Such fillers include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605; 3,814,717; 4,143,018; 4,209,434; 4,360,605 and 4,376,835. Such reactive fillers may be incorporated to modify the handling characteristics or to affect the setting properties of the ultimate compostion.

The reactive filler is preferably a finely divided reactive filler. The filler should be sufficiently finely-divided so that it can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

For good handling properties the fillers used are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses.

Most preferred of the acid reactive fillers are those that release fluoride. Fluoride releasing glasses, in addition to providing good handling and final composition properties as discussed above, provide the benefit of long-term release of fluoride in use, for example in the oral cavity. Fluoroaluminosilicate glasses are particularly preferred. Suitable acid reactive fillers are also available from a variety of commercial sources familiar to those skilled in the art. For example, suitable fillers can be obtained from a number of commercially available glass ionomer cements, such as "GC Fuji LC" and "Kerr XR" ionomer cement. Mixtures of fillers can be used if desired.

If desired, the acid reactive filler can be subjected to a surface treatment. Suitable surface treatments include acid washing, treatment with phosphates, treatment with chelating agents such as tartaric acid, treatment with a silane or silanol coupling agent. Particularly preferred acid reactive fillers are silanol treated fluoroaluminosilicate glass fillers, as described in U.S. Pat. No. 5,332,429 the disclosure of which is expressly incorporated by reference herein.

Non-acid reactive fillers may be selected from one or more of any material suitable for incorporation in compositions used for medical applications, such as fillers currently used in dental restorative compositions and the like. The filler is finely divided and preferably has a maximum particle diameter less than about 10 micrometers and an average particle diameter less than about 1.0 micrometers. More preferably, the filler has a maximum particle diameter less than about 1.0 micrometers and an average particle size of diameter less than about 0.1 micrometer. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable non-acid reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable non-reactive organic filler particles include filled or unfilled pulverized polycarbonates, polyepoxides, and the like. Preferred non-acid reactive filler particles are quartz, submicron silica, and non-vitreous microparticles of the type described in U.S. Pat. No. 4,503,169. Mixtures of these non-acid reactive fillers are also contemplated, as well as combination fillers made from organic and inorganic materials.

Preferably the surface of the filler particles is treated with a coupling agent in order to enhance the bond between the filler and the polymerizable resin. The use of suitable coupling agents include gamma-methacryloxypropyltrimethoxysilane, gamma-mercaptopropyltriethoxysilane, gamma-aminopropyltrimethoxysilane, and the like.

If desired, the compositions of the invention can contain adjuvants such as cosolvents, pigments, inhibitors, accelerators, viscosity modifiers, surfactants, rheology modifiers, colorants, medicaments and other ingredients that will be apparent to those skilled in the art. Optionally, the compositions may contain stabilizers.

Cosolvents useful in the present invention include, but are not limited to, low molecular weight organic solvents. The word "cosolvent", as used herein refers to a material that aids in the dissolution of materials in the composition, in order to form a homogeneous composition. Examples of suitable cosolvents include ethanol, propanol, and glycerol.

The compositions of this invention can be used in a variety of applications in the dental or medical fields in which a material is desired that will adhere well to the surrounding tooth or bone structure. For instance, these compositions can be used as dental restoratives, liners, bases, cements, sealants and as dental or orthodontic adhesives. The present compositions are preferably provided initially as a one-part paste composition.

The present invention will be further understood in view of the following examples which are merely illustrative and not meant to limit the scope of the invention. Unless otherwise indicated, all parts and percentages are by weight.

Water Uptake Test

Water uptake was measured by forming each composition into disks 20 mm in diameter and 1 mm thick. Both sides of each disk were covered with polyethylene terephthalate ("PET") film and light cured for 30 seconds on each side using two oppositely-disposed 3M™ Visilux™ 2 Visible Light Curing Units with about a 1 cm distance between the output end of the light guide and the sample. The film was then removed and the exposed samples allowed to cure for 1 hour at 37° C./95% relative humidity ("RH"). Each disk was weighed and placed in a glass jar to which was added 25 mL of deionized water. The sample was maintained at 37° C. for a specified time period.

At the specified time, the sample was removed from the jar, the superficial water was removed using a facial tissue or cotton and the sample was immediately weighed. The weight was recorded and the sample was returned to the water in the sample jar. At periodic designated intervals, the above procedure was repeated and the sample weight recorded. At each specified time interval, water uptake for 3 samples of each composition was measured and the average reported in grams per 100 grams of cured composition.

The present invention will be further understood in view of the following examples which are merely illustrative and not meant to limit the scope of the invention. Unless otherwise indicated, all parts and percentages are by weight and all molecular weights are weight average molecular weights.

PREPARATORY EXAMPLE 1

Treated Fluoroaluminosilicate Glass

The ingredients set out below in TABLE 1 were mixed, melted in an arc furnace at about 1350–1450° C., poured from the furnace in a thin stream and quenched using chilled rollers to provide an amorphous single-phase fluoroaluminosilicate glass.

TABLE 1

| Ingredient | Parts |
| --- | --- |
| $SiO_2$ | 37 |
| $AlF_3$ | 23 |
| $SrCO_3$ | 20 |
| $Al_2O_3$ | 10 |
| $Na_3AlF_6$ | 6 |
| $P_2O_5$ | 4 |

The glass was ball-milled to provide pulverized frits with surface areas shown in Table 2 measured using the Brunauer, Emmet and Teller (BET) method.

A silanol solution was prepared by mixing together the required parts of gamma-methacryloxypropyl trimethoxysilane ("A-174", OSi Specialties, Inc.) as defined in Table 2, 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated dried powder was sieved through a 60 micrometer mesh screen.

TABLE 2

| Preparatory Example | Glass Surface Area ($m^2/g$) | Parts A-174 |
| --- | --- | --- |
| 1A | 3.20 | 2.43 |
| 1B | 7.83 | 2.95 |
| 1C | 3.85 | 1.51 |
| 1D | 3.85 | 5.19 |
| 1E | 11.50 | 1.51 |

PREPARATORY EXAMPLE 2

2A) Treated OX-50

A-174 (3.7 g) was added with stirring to 50 g of deionized water acidified to pH 3–3.3 by dropwise addition of trifluoroacetic acid. The resultant mixture was stirred at about 25° C. for 1 hour at which time 95 g of OX-50 were added to the mixture with continued stirring for 4 hours. The slurry was poured into a plastic-lined tray and dried at 35° C. for 36 hours. The silanol treated dried powder was sieved through a 74 micrometer mesh screen.

2B) Treated Colloidal Silica (OX-50)

A silanol solution was prepared by mixing together 5.52 parts of A-174, 3.68 parts of methanol, 0.5 parts of acetic acid, and 0.8 parts of deionized water. Colloidal silica (OX-50) (23 parts) was charged to a solids blender. While mixing the colloidal silica (OX-50) the silanol solution was pumped into the solids blender over the course of 30 minutes. The treated powder was discharged from the solids blender into plastic-lined trays, and dried for three hours, 45 minutes at 67° C. and then for one hour, 15 minutes at 100° C. The treated dried powder was sieved through a 74 μm screen.

PREPARATORY EXAMPLE 3

Treated Zirconia:Silica Filler 25.5 Parts silica sol ("LUDOX" LS, E.I. duPont de Nemours & Co.) were acidified by the rapid addition of 0.255 parts concentrated nitric acid. In a separate vessel, 12.9 parts ion-exchanged zirconyl acetate (Magnesium Elecktron Inc.) were diluted with 20 parts deionized water and the resultant solution acidified with 0.255 parts concentrated nitric acid. The silica sol was pumped into the stirred zirconyl acetate solution and mixed for one hour while filtering the stirred mixture through "CUNO" 5 micrometer and 1 micrometer filters (Commercial Intertech Corp.). The stirred, filtered mixture was further filtered though a 1 micrometer "HYTREX" filter (Osmonics, Inc.) followed by a 0.22 micrometer "BALSTRON" filter (Balston Inc.). The filtrate was poured into trays to a depth of about 25 mm and dried at 65° C. in a forced air oven for about 24 hours. The resultant dried material was removed from the oven and tumbled through a rotary tube furnace (Harper Furnace Corporation) preheated to 600° C. to provide 21 parts of calcined microparticles. The calcined microparticles were comminuted in a tumbling ball mill until all of the microparticles were less than 10 micrometers in particle diameter. 0.3 Part portions of the milled microparticles were placed in ceramic saggers and fired in an electric kiln (Harper Furnace Corporation) in air at 825° C. for 1 hour. The fired microparticles were allowed to cool in air. The cooled microparticles were slurried in hydrolyzed A-174 silane at a ratio of 11.1 parts silane to 100 parts microparticles, dried in a forced air oven and screened through a 74 micrometer mesh screen.

PREPARATORY EXAMPLE 4

Treated Quartz Filler

A silanol solution was prepared by mixing together 2.64 parts of A-174, 0.0324 parts of acetic acid, and 52.7 parts of deionized water. This mixture was stirred for 45 minutes at approximately 30° C. To this silanol solution was added 50.6 parts of quartz (average particle size =2.7 μm) and 2.1 parts of Cab-O-Sil-M5 (Cabot Corporation). This slurry was mixed for 2 hours at ambient conditions. The slurry was poured into plastic-lined trays and dried for 24 hours at 38° C. The treated dried powder was crushed, sieved through a 1 mm screen, and dried further for 2 hours at 110° C. The powder was crushed and screened a second time through a 100 μm screen, and dried further for 16 hours at 38° C. The treated powder was sieved a final time through a 220 μm screen.

PREPARATORY EXAMPLE 5

Preparation of Polymerizable Component "A1" or "CDMA"

Citric acid (400 g) was dissolved in 2 L of tetrahydrofuran ("THF") in a reaction vessel fitted with a mechanical stirrer, condenser, addition funnel and air inlet tube. To the resultant homogenous solution was added 0.52 g butylated hydroxytoluene ("BHT"), 0.5 g of triphenylantimony ("TPS") and 0.98 g dibutyltin dilaurate ("DBTDL"). Dry air was introduced into the reaction mixture through the inlet tube. 2-Isocyanatoethyl methacrylate ("IEM"; 161.5 g; 1.04 moles) was added dropwise through the addition funnel so as to maintain the reaction temperature at about 40° C. The reaction was followed by infrared spectroscopy ("IR"). After all the IEM had been added and the IR spectrum no longer showed the presence of isocyanate group, the solvent was removed under vacuum from the reaction mixture and the resultant viscous liquid was dried. Nuclear magnetic resonance spectroscopy ("NMR") confirmed the presence of added methacrylate functionalities and the retention of carboxy groups.

PREPARATORY EXAMPLE 6

Preparation of Polymerizable Component "A2"

Polyacrylic acid (8.64 g; molecular weight 2,000) and 75 mL THF were added to a reaction flask equipped with a stirrer, condenser, addition funnel and air inlet tube. After stirring at a bath temperature of 50–70° C. for 2–3 hours, a cloudy solution was obtained. The temperature of the bath was maintained at 40–50° C. and a solution containing 0.093 g BHT, 0.093 g TPS and 0.64 g DBTDL in 5 mL of dry THF was added to the reaction mixture. IEM (9.3 g) was added dropwise through the addition funnel over a period of 1 hour. The mixture was allowed to stir until the IR spectrum showed complete disappearance of the isocyanate band at which time the reaction mixture was poured into petroleum ether. A white, solid polymer precipitated and was isolated by filtration, washed and dried under vacuum.

PREPARATORY EXAMPLE 7

Preparation of Metal Fluorocomplexes

Metal fluorocomplexes DI–DXI were independently prepared by dissolving the quantity of the carboxylic acid complexing agent set out in TABLE 2 in water. For Complex nos. DI–DIX, zinc fluoride powder was slurried with each aqueous solution for about one-half hour, after which time the slurry was poured into a shallow tray and dried at 55° C. overnight. Each complex was then sieved through a 100 micrometer mesh screen to provide a free-flowing powder. Complex nos. DX and DXI were prepared as detailed for the zinc complexes except that 20 g aluminum trifluoride and 20 g zirconium tetrafluoride respectively were substituted for the zinc fluoride and the resultant complexes were sieved through a 74 micrometer mesh screen. Complex no. DXII was prepared by mixing the zinc fluoride with a mixture of acetoacetoxyethylmethacrylate ("AAEM"; Eastman Chemicals, TN), 10 g ethanol and 5 g deionized water. The resultant mixture was allowed to stir for 12 hours at ambient temperature. The solid was then collected by filtration and dried under vacuum at 45° C. for 12 hours. The dried solid was crushed with a mortar and pestle to yield a fine powder of Complex no. DXII.

TABLE 3

| Complex | Complexing Agent | | Water | $ZnF_2$ |
|---|---|---|---|---|
| No. | Type | Amount (g) | (g) | (g) |
| DI | Tartaric acid | 20 | 20 | 20 |
| DII | Tartaric acid | 20 | 20 | 80 |
| DIII | Tartaric acid | 30 | 20 | 20 |
| DIV | Tartaric acid | 20 | 20 | 30 |
| DV | N-methacryloyl glutamic acid | 20 | 20 | 20 |
| DVI | Itaconic acid | 20 | 300 | 80 |
| DVII | Itaconic acid | 20 | 300 | 40 |
| DVIII | Itaconic acid | 25 | 350 | 25 |
| DIX | Itaconic acid | 30 | 380 | 20 |
| DX | Tartaric acid | 20 | 20 | — |
| DXI | Tartaric acid | 20 | 20 | — |
| DXII | AAEM | 20 | — | 10 |

PREPARATORY EXAMPLE 8

Zinc-fluoro ($ZnF_2$) Complex

The zinc-fluoro complex salt was prepared by slurrying 80 g zinc fluoride powder in a solution made up from 80 g of CDMA and 80 g of glycerol dimethacrylate ("GDMA"). The slurrying process was carried out at 45° C. in the presence of an air bleed for seven days. The viscous slurry obtained was used for preparing the pastes of Examples 8A–8D.

PREPARATORY EXAMPLE 9

Preparation of Hydrophilic Component "C1"

A glass reaction flask equipped with magnetic stirrer, two addition funnels connected to peristaltic pumps, thermometer, gas inlet tube and reflux condenser was charged with 300 mL of dry THF. One addition funnel was charged with a solution of ethylmethacrylate (18.24 g; 0.16 moles), acrylic acid (28.8 g; 0.4 moles), N-vinylpyrrolidone ("NVP"; 26.98 g; 0.24 moles) and THF to a volume of 200 mL. The second addition funnel was charged with a solution of 0.82 g azobisisobutyronitrile ("AIBN") in 60 mL THF. Both solutions were purged with dry nitrogen for 15 minutes. The reaction vessel was heated to 60° C. and the charges from both addition funnels were added via the peristaltic pumps over a course of 6 hours. After addition was complete, the reaction was stirred at 60° C. overnight. Then 300 mL of dry dimethylformamide ("DMF") was added to the reaction vessel and the temperature lowered to 40° C. BHT (0.094 g), TPS (0.094 g) and DBTDL (0.644 g) were added to the reaction mixture and the nitrogen in the inlet tube was switched to dry air. A solution of IEM (18.6 g; 0.12 mole) in 45 mL THF was added dropwise to the reaction mixture over 2 hours. The reaction mixture was then allowed to stir at 40° C. for an additional hour. The solvents were partially removed under vacuum to reduce the volume to about one-half of the original and the resultant solution poured into ethyl acetate. The precipitated polymer was collected by filtration, washed and dried under vacuum.

PREPARATORY EXAMPLE 10

Preparation of Hydrophilic Component "C2"

A glass reaction flask equipped with magnetic stirrer, two addition funnels connected to peristaltic pumps, thermometer, gas inlet tube and reflux condenser was charged with 500 mL of dry THF. One addition funnel was charged with a solution of ethylmethacrylate (34.25 g; 0.3 moles), acrylic acid (50.4 g; 0.7 moles) and THF to a volume of 200 mL. The second addition funnel was charged with a solution of 0.82 g AIBN in 60 mL THF. The solutions were purged with dry nitrogen for 15 minutes. The reaction vessel was heated to 60° C. and the charges from both addition funnels were added via the peristaltic pumps over a course of 6 hours. After addition was complete, the reaction was stirred at 60° C. overnight. Then the reaction temperature was lowered to 35° C. BHT (0.165 g), TPS (0.165 g) and DBTDL (1.13 g) were added to the reaction mixture and the nitrogen in the inlet tube was switched to dry air. A solution of IEM (32.55 g; 0.21 moles) in 200 mL THF was added dropwise to the reaction mixture over 2 hours. The reaction mixture was then allowed to stir at 35–40° C. for an additional hour. The solvents were partially removed under vacuum to reduce the volume to about one-third of the original and the resultant solution poured into ethyl acetate. The precipitated polymer was collected by filtration, washed and dried in under vacuum.

PREPARATORY EXAMPLE 11

Preparation of Hydrophilic Component "C3"

A glass reaction flask equipped with magnetic stirrer, two addition funnels connected to peristaltic pumps, thermometer, gas inlet tube and reflux condenser was charged with 500 mL of dry THF. One addition funnel was charged with a solution of ethylmethacrylate (17.12 g; 0.15 moles), acrylic acid (50.4 g; 0.7 moles), methacrylic acid (12.9 g; 0.15 moles) and THF to a volume of 200 mL. The second addition funnel was charged with a solution of 0.82 g of AIBN in 60 mL THF. Both solutions were purged with dry nitrogen for 15 minutes. The reaction vessel was heated to 60° C. and the charges from the addition funnels were added via the peristaltic pumps over a course of 6 hours. After the addition was complete, the reaction was stirred at 60° C. overnight. Then the reaction temperature was lowered to 350° C. BHT (0.165 g), TPS (0.165 g) and DBTDL (1.13 g) were added to the reaction mixture. The nitrogen in the inlet tube was switched to dry air. A solution of IEM (32.55 g; 0.21 mole) in 200 mL THF was added dropwise to the reaction mixture over 2 hours. The mixture was then allowed to stir at 35–40° C. for an additional hour. The solvents were partially removed under vacuum to reduce the volume to about one-third of the original and the resultant solution poured into ethyl acetate. The precipitated polymer was collected by filtration, washed and dried under vacuum.

PREPARATORY EXAMPLE 12

Preparation of Hydrophilic Component "C4"

A glass reaction flask equipped with magnetic stirrer, two addition funnels connected to peristaltic pumps, thermometer, gas inlet tube and reflux condenser was charged with 210 mL of dry THF. One addition funnel was charged with a solution of acrylic acid (50.4 g; 0.7 moles), NVP (33.3 g; 0.3 moles) and THF to a volume of 250 mL. The second addition funnel was charged with a solution of 0.82 g AIBN in 60 mL THF. Both solutions were purged with dry nitrogen for 15 minutes. The reaction vessel was heated to 60° C. and the charges from both addition funnels were added via the peristaltic pumps over a course of 4 hours. After addition was complete, 22 mL of dry DMF was added and the reaction was stirred at 60° C. overnight. The reaction temperature was then lowered to 35° C. BHT (0.15 g), TPS (0.15 g) and DBTDL (1.03 g) were added to the reaction mixture and the nitrogen in the inlet tube was switched to dry air. A solution of IEM (32.55 g; 0.21 mole) in 200 mL THF was added dropwise to the reaction mixture over 2 hours. The reaction mixture was then allowed to stir at 35–40° C. for an additional 24 hours. The solvents were partially removed under vacuum to reduce the volume to about one-third of the original and the resultant solution poured into ethyl acetate. The precipitated polymer was collected by filtration, washed and dried under vacuum.

EXAMPLE 1

Pastes were prepared by mixing the ingredients shown in TABLE 4. The specified quantities of polymerizable component A1 of PREPARATORY EXAMPLE 5 ("PE 5"), glycerol dimethacrylate ("GDMA"; Rohm Tech, Inc., Malden, Mass.) and 1.1 g or no poly(N-vinyl pyrrolidone) ("PNVP"; Plastone K-29/31, International Specialty Products, Wayne, N.J.) were thoroughly mixed with 0.095 g camphorquinone ("CPQ") and 0.37 g ethyl(4-dimethylamino)benzoate ("EDMAB"). A portion of the resultant mixture was combined with the specified amounts of the glass of PREPARATORY EXAMPLE 1A ("PE1A")+ 2% OX-50 of PREPARATORY EXAMPLE 2A ("PE2A") and 4 g or no Complex DI from PREPARATORY EXAMPLE 7 ("PE7") TABLE 3. The pastes were either hand-mixed or mechanically mixed using a double planetary mixer.

TABLE 4

| Run No. | Component A1 of PE5 (g) | GDMA (g) | PNVP (g) | Glass of PE1A + 2% OX-50 of PE2A (g) | Complex DI of PE7 (g) |
| --- | --- | --- | --- | --- | --- |
| 1 | 7.0 | 13.9 | 1.1 | 74.0 | 4 |
| 2 | 7.0 | 13.9 | 1.1 | 78.0 | 0 |
| 3 | 7.3 | 14.7 | 0 | 74.0 | 4 |
| 4 | 7.3 | 14.7 | 0 | 78.0 | 0 |

Water uptake of each composition in TABLE 4 as well as that of Dyract™ Light Cured Compomer ("Dyract"; Dentsply International Inc.) was measured on day 7 and day 14 using the procedure described in the Water Uptake Test. The results are set out in TABLE 5.

Incremental fluoride release of each composition was measured after 3 days and compared with that of Dyract. Disks of each composition were prepared and cured as described for the Water Uptake Test. Each disk was placed in ajar containing 25 mL of deionized water at 37° C.

A fluoride-selective electrode, Orion Model 96-09-00 (from Orion Research Inc., Cambridge, Mass.) was used to quantify the amount of fluoride ion released from the sample in the water. The electrode was calibrated using Fluoride Activity Standards #940907 and #040908, a 100 parts per million ("ppm") and a 10 ppm respectively, fluoride standard fluid (both from Orion Research Inc.).

For the measurement of fluoride ions released into the water, 10 mL of the sample solution was transferred on the day specified to a 60 mL beaker and 10 mL of TISAB solution (total ionic strength adjustment buffer; Orion Research Inc., Cambridge, Mass.) was added to the beaker. The contents were mixed for 10 seconds. The calibrated fluoride-selective electrode was placed in the solution and the ppm $F^-$ were recorded and converted to micrograms of $F^-$ per $cm^2$ of the cured disk. The residual liquid was then removed from the sample jar and replaced with a fresh 25 mL quantity of deionized water. The sample jar was transferred to a 37° C. oven for the specified interval in days, at which time, the sample jar was removed from the oven and the ppm $F^-$ released during that interval were measured as described above. Micrograms of $F^-$ per $cm^2$ of the cured disk were again calculated and these values were reported as a function of time of storage in the water. Fluoride release values for 3 samples of each composition were measured and the average recorded. The results are set out in TABLE 4.

TABLE 5

| | Water Uptake in g/100 g of Cured Composition Measured on Day | | µg/cm² F⁻ Released |
|---|---|---|---|
| Run No. | 7 | 14 | After 3 Days |
| 1 | 1.7 | 1.9 | 43.38 |
| 2 | 1.9 | 2.1 | 26.03 |
| 3 | 1.5 | 1.8 | 34.70 |
| 4 | 1.6 | 1.9 | 19.52 |
| Dyract | 1.1 | 1.2 | 2.2 |

The data in TABLE 5 show that the compositions of Run nos. 1–4 of the invention in general took up significantly more water than a commercial one-paste fluoride releasing material, Dyract, and correspondingly released much higher quantities of fluoride. Furthermore, the incremental fluoride release data show that although a fluoroaluminosilicate glass in a hydrophilic resin matrix exhibited enhanced fluoride release compared to Dyract, the addition of a metallo-fluorocomplex to the compositions of Run nos. 1 and 3 substantially increased the fluoride release.

EXAMPLE 2

Pastes were prepared by mixing the ingredients shown in TABLE 6. The specified quantities of polymerizable component A1 of PREPARATORY EXAMPLE 5, GDMA and component C were thoroughly mixed with CPQ at a concentration of 0.42 parts per hundred and EDMAB at a concentration of 1.65 parts per hundred. A portion of the resultant mixture was combined with the specified amounts of the glass of PE1A+2% OX-50 of PE2A and the Complex of PREPARATORY EXAMPLE 7 as outlined in TABLE 6. The pastes were either hand-mixed or mechanically mixed using a double planetary mixer.

For determination of compressive strength ("CS") and diametral tensile strength ("DTS"), the composition of each run no. was packed into a 4 mm inside diameter glass tube, capped with silicone rubber plugs and axially compressed at about 0.28 MPa for 15 minutes, then light cured for 80 seconds by exposure to two oppositely-disposed Visilux units. Each sample was then irradiated for 30 seconds using a Dentacolor XS unit (Kulzer). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured according to ADA ("American Dental Association") specification No. 9 and ADA specification No. 27 respectively.

TABLE 6

| Run No. | Component A1 PE5 (g) | GDMA (g) | Component C Ex. | Component C Amount (g) | Glass of PE1A + 2% OX-50 of PE2A (g) | Complex of PE7 No. | Complex of PE7 Amount (g) | CS (MPa) | DTS (MPa) |
|---|---|---|---|---|---|---|---|---|---|
| 1 | 7.15 | 14.30 | PE9 | 0.55 | 76 | DI | 2 | 346 | 44.8 |
| 2 | 7.00 | 13.90 | PE10 | 1.1 | 76 | DI | 2 | 367 | 54.8 |
| 3 | 7.15 | 14.30 | PE10 | 0.55 | 76 | DI | 2 | 376 | 50.1 |
| 4 | 7.15 | 14.30 | PE11 | 0.55 | 76 | DI | 2 | 378 | 55.5 |
| 5 | 7.00 | 13.90 | PE11 | 1.10 | 76 | DV | 2 | 288 | 37.6 |
| 6 | 7.00 | 13.90 | PNVP | 1.10 | 76 | DI | 2 | 368 | 57.7 |
| 7 | 7.00 | 13.90 | PNVP | 1.10 | 74 | DI | 4 | 341 | 42.2 |
| 8 | 7.00 | 13.90 | PNVP | 1.10 | 72 | DI | 6 | 348 | 43.6 |
| 9 | 7.00 | 13.90 | PNVP | 1.10 | 76 | DV | 2 | 338 | 47.6 |
| 10 | 7.00 | 13.90 | PNVP | 1.10 | 72 | DV | 6 | 336 | 34.5 |
| 11 | 7.00 | 13.90 | PNVP | 1.10 | 72 | DI | 6 | 341 | 52.3 |
| 12 | 7.00 | 13.90 | PE10 | 1.10 | 76 | DI | 2 | 373 | 50.2 |
| 13 | 7.00 | 14.0 | PE12 | 0.52 | 78 | DI | 4 | 290 | 48.3 |

The CS and DTS of the paste compositions of Run nos. 1–13 were superior to the mechanical properties of two commercial fluoride releasing materials, 3M™ Vitremer™ Glass Ionomer Core Build-up Restorative ("Vitremer"; 3M) with a CS of 214 MPa and Dyract with a CS of 262 MPa.

Water uptake of the compositions of Run nos. 2, 4 and 6 in TABLE 6 as well as that of Dyract was measured on days 5, 12 and 28 using the procedure described in the Water Uptake Test. The results are set out in TABLE 7.

Incremental fluoride release of the compositions of Run nos. 1, 2, 6, 9 and 10 as well as that of Dyract and Vitremer was measured on days 4, 8, 14, 21 and 27 using the procedure described in EXAMPLE 1. The results are set out in TABLE 7.

TABLE 7

| | Water Uptake in g/100 g of Cured Composition Measured on Day | | | Incremental F⁻ Release in µg/cm² Measured on Day | | | | |
|---|---|---|---|---|---|---|---|---|
| Run No. | 5 | 12 | 28 | 4 | 8 | 14 | 21 | 27 |
| 1 | — | — | — | 28.3 | 17.6 | 36.4 | 25.3 | 20.8 |
| 2 | 1.6 | 2.03 | 2.47 | 17.1 | 14.2 | 20.5 | 20.8 | 19.3 |
| 4 | 1.69 | 2.09 | 2.56 | — | — | — | — | — |
| 6 | 1.6 | 2.17 | 2.54 | 19.1 | 16.5 | 23.4 | 18.7 | 19.5 |
| 9 | — | — | — | 18.2 | 15.3 | 21.2 | 22.8 | 20.4 |
| 10 | — | — | — | 52.1 | 31.8 | 48.1 | 49.1 | 35.6 |
| Dyract | 0.65 | 1.05 | 1.26 | 8.1 | 10.7 | 13.4 | 13.1 | 16.9 |
| Vitremer | — | — | — | 33.3 | 17.6 | 36.4 | 27.5 | 22.1 |

The data in TABLE 7 show that compositions of the invention exhibited higher water uptake and higher fluoride release compared to a commercial one-paste fluoride releasing material, Dyract. The rate of fluoride release was comparable to a water-based powder:liquid glass ionomer, Vitremer.

EXAMPLE 3

Three resin mixtures were prepared by mixing together 7.0 g polymerizable component A1 of PREPARATORY EXAMPLE 5, 13.9 g GDMA, 1.1 g PNVP, 0.095 g CPQ and 0.37 g EDMAB to provide a homogeneous mixture. Pastes were then compounded by adding to each mixture 74 g of a blend of the glass of PE1A, 2% OX-50 of PE2A and 4.0 g of the designated Complex from TABLE 3. All three resultant pastes were stable at room temperature whereas control pastes prepared using untreated zinc fluoride showed substantial thickening on standing and became crumbly after 24 hours.

Using the procedure described in EXAMPLE 1, incremental fluoride release of the compositions of Run nos. 1–3 was measured and compared with that of Dyract and Vitremer. The results are set out in TABLE 8.

Cumulative fluoride release was measured on disks of the compositions prepared and cured as described for the Water Uptake Test. Each disk was placed in a jar of phosphate buffer prepared by mixing 0.7 g $KH_2PO_4$ and 0.71 g $Na_2HPO_4$ in 1 liter of deionized water to provide a 0.01M solution having a pH of 6.8–7.0 at 37° C.

A calibrated fluoride-selective electrode as described for incremental fluoride release in EXAMPLE 1 was placed in the buffer solution containing the disk on the days designated in TABLE 9 and ppm $F^-$ recorded. Micrograms of $F^-$ per $cm^2$ of the cured disk were then calculated and these values were reported as a function of time of storage in the buffer. Fluoride release values for 3 samples of each composition were measured and the average reported in TABLE 9. The composition of Run no. 4 showed no measurable fluoride release.

TABLE 8

| Run No. | Complex from Table 3 | Incremental $F^-$ Released in $\mu g/cm^2$ Measured on Day | | | | | | | | |
|---|---|---|---|---|---|---|---|---|---|---|
| | | 1 | 2 | 3 | 4 | 5 | 6 | 7 | 14 | 21 |
| 1 | DII | 79.53 | 28.20 | 32.53 | 18.08 | 17.35 | 14.46 | 8.68 | 35.43 | 20.24 |
| 2 | DI | 79.53 | 20.24 | 21.69 | 13.01 | 9.40 | 10.12 | 7.23 | 27.83 | 17.21 |
| 3 | DVII | 79.53 | 36.15 | 26.75 | 20.24 | 16.63 | 15.91 | 10.85 | 44.54 | 22.27 |
| Dyract | — | 7.95 | 1.95 | 2.02 | 1.37 | 2.46 | 1.45 | 1.45 | 4.55 | 3.54 |
| Vitremer | — | 65.07 | 16.63 | 13.01 | 10.12 | 8.68 | 6.51 | 5.06 | 27.83 | 16.70 |

The incremental fluoride release results in TABLE 8 show that paste compositions of the invention containing a hydrophilic matrix showed much higher fluoride release than a commercial one-paste fluoride-releasing material, Dyract. The amount of fluoride released was comparable to a water-based powder:liquid glass ionomer, Vitremer.

EXAMPLE 4

Four resin mixtures were prepared by mixing 7.35 g polymerizable component A1 of PREPARATORY EXAMPLE 5, 14.65 g GDMA, 0.095 g CPQ and 0.37 g EDMAB to provide a homogeneous mixture. Pastes were then compounded by adding to each mixture the filler type and amount and 2.0 g or none of Complex D1 from TABLE 3 as set out in TABLE 9.

TABLE 9

| Run No. | Filler | | Complex | Cumulative $F^-$ Release in $\mu g/cm^2$ Measured on Day | | |
|---|---|---|---|---|---|---|
| | Type | Amount (g) | DI PE7 (g) | 0 | 7 | 24 |
| 1 | Glass of PE1A + 2% OX-50 of PE2A | 78 | 0 | 1 | 30 | 45 |
| 2 | Glass of PE1A + 2% OX-50 of PE2A | 76 | 2 | 2 | 45 | 95 |
| 3 | PREPARATORY EXAMPLE 3 | 76 | 2 | 1 | 20 | 35 |
| 4 | PREPARATORY EXAMPLE 3 | 78 | 0 | — | — | — |

The data in TABLE 9 show that the incorporation of a fluorocomplex increased the fluoride release of the compositions of Run nos. 2 and 3. This effect was exhibited even when no other acid-reactive filler was incorporated into the system. Thus both Run nos. 3 and 4 contained a non-acid reactive filler, but only Run no. 3, which contained a fluorocomplex salt, showed appreciable fluoride release.

EXAMPLE 5

A stock liquid was made up by blending 219 g polymerizable component A1 of PREPARATORY EXAMPLE 5, 400 g GDMA, 30 g PNVP, 11 g EDMAB and 2.8 g CPQ. Six pastes were then formulated using 12.6 g of the stock liquid, 43.8 g of the glass of PE1A, 1.2 g of OX-50 of PE2A and 2.4 g of the Complex of PREPARATORY EXAMPLE 7 identified in TABLE 10. The CS and DTS of the compositions were measured according to the procedure detailed in EXAMPLE 2.

TABLE 10

| Run. No. | Complex of Ex. 3 | CS (MPa) | DTS (MPa) |
|---|---|---|---|
| 1 | DI | 324 | 53.8 |
| 2 | DIII | 324 | 51.7 |
| 3 | DIV | 331 | 51.0 |
| 4 | DVII | 310 | 53.1 |
| 5 | DVIII | 303 | 48.3 |
| 6 | DIX | 317 | 55.2 |

The data in TABLE 10 show that one-paste compositions containing a hydrophilic resin matrix and zincfluorocomplexes provided cured specimens exhibiting excellent mechanical properties.

EXAMPLE 6

Two pastes were formulated using 12.4 g of the stock liquid of EXAMPLE 5, 43.8 g of the glass of PE1A, 1.2 g of OX-50 of PE2A and 2.4 g of the aluminumfluorocomplex or the zirconiumfluorocomplex of PREPARATORY EXAMPLE 7. A third paste was formulated as described for the first two pastes, except that 12.6 g of the stock liquid of EXAMPLE 5 was used and the fluorocomplex was DXII. CS and DTS was measured according to the procedure described in EXAMPLE 2 and incremental fluoride release was measured according to the procedure detailed in EXAMPLE 1.

TABLE 11

| Run No. | Complex of PE7 | CS (MPa) | DTS (MPa) | Incremental F$^-$ Release in $\mu g/cm^2$ Measured on Day 1 | 7 |
|---|---|---|---|---|---|
| 1 | DX | 304 | 52.2 | 24.5 | 4.8 |
| 2 | DXI | 312 | 51.7 | 44.8 | 14.2 |
| 3 | DXII | 345 | 50.3 | 88.9 | 13.1 |

The data in TABLE 11 show additional examples of pastes containing a hydrophilic matrix and various metallofluorocomplexes. These pastes exhibited excellent mechanical properites as well as very high fluoride release.

EXAMPLE 7

A stock solution was prepared by dissolving 40 g GDMA, 3 g PNVP, 1.1 g benzoyl peroxide and 0.088 g BHT. Then 8.4 g of the stock solution was combined with 4.2 g of the polymerizable component A1 of PREPARATORY EXAMPLE 5. The resulting homogeneous liquid was combined with 43.8 g of the glass of PE1A, 1.2 g OX-50 of PE2A and 2.4 g of Complex DI of PREPARATORY EXAMPLE 7 to provide a Paste "A".

Three Paste "B" formulations were prepared by combining 43.8 g of the glass of PE1A, 1.2 g OX-50 of PE2A and 2.4 g of Complex DI of PREPARATORY EXAMPLE 7 with 12.6 g of the ingredients set out below in TABLE 12.

TABLE 12

| Paste B Liquid Ingredients | Paste B1 (g) | Paste B2 (g) | Paste B3 (g) |
|---|---|---|---|
| CD-541[1] | 47.5 | — | — |
| PEG$_{600}$ DMA[2] | — | 23.7 | — |
| UDMA[3] | — | 23.7 | 35 |
| PNVP | 2.5 | 2.5 | 2.5 |
| HEMA[4] | 10 | 10 | 12.5 |
| DMAPE[5] | 1.5 | 1.5 | 1.5 |

[1]Sartomer, Exton, PA.
[2]Polyethyleneglycol-600 dimethacrylate (Sartomer).
[3]Urethane dimethacrylate (Rohm Tech, Inc., Malden, MA).
[4]2-Hydroxyethyl methacrylate.
[5]4-(Dimethylamino)phenethanol.

Compositions were prepared by combining four parts of Paste A with one part of Paste B1, B2 and B3 respectively. Set time was measured according to ISO specification 9917 and CS and DTS were measured according to the procedure described in EXAMPLE 2.

TABLE 13

| Run. No. | Paste B | Set Time (min.:sec.) | CS (MPa) | DTS (MPa) |
|---|---|---|---|---|
| 1 | B1 | 4:00 | 310 | 44.8 |
| 2 | B2 | 3:30 | 303 | 37.9 |
| 3 | B3 | 2:30 | 255 | 27.6 |

The data in TABLE 13 illustrate two-paste compositions containing a hydrophilic resin matrix and a fluorocomplex that cured upon mixing to yield materials exhibiting good physical properties and set times that were clinically acceptable.

EXAMPLES 8A–8D

Four dental restorative filling materials were prepared with a photo-polymerizable dental resin and inorganic fillers per Table 14. The resin consisted of 61.14% GMDA, 32.23% CDMA of Preparatory Example 5, 4.34% PNVP, 1.76% ethyl 4-dimethylamino benzoate (EDMAB), 0.45% camphorquinone (CPQ), 0.09% BHT. The treated colloidal silica (OX-50) is of Preparatory Example 2B and the treated fluoroaluminosilicate glass is of Preparatory Example 1A.

TABLE 14

| Example | Resin (wt. %) | ZnF2 Complex of Preparatory Example 8 (wt. %) | Treated Colloidal Silica (OX-50) of Preparatory Example 2B (wt. %) | Treated Fluoroalumino-silicate Glass of Preparatory Example 1A (wt. %) | Pigments (wt. %) |
|---|---|---|---|---|---|
| 8A | 15.51 | 4.00 | 1.68 | 78.74 | 0.08 |
| 8B | 15.28 | 3.91 | 1.65 | 79.08 | 0.08 |
| 8C | 16.87 | 4.11 | 1.75 | 77.17 | 0.08 |
| 8D | 14.25 | 4.07 | 1.72 | 79.87 | 0.08 |

EXAMPLES 9A–9F

Six dental restorative filling materials were prepared with a photo-polymerizable dental resin (60.99% GDMA, 32.40% CDMA of Preparatory Example 5, 4.29% PNVP, 1.01% Tinuvin-P™ (a stabilizer available from Ciba-Geigy), 0.98% EDMAB, 0.25% CPQ, 0.09% BHT) and inorganic fillers per Table 15. The treated colloidal silica (OX-50) is of Preparatory Example 2B and the treated fluoroaluminosilicate glasses are of Preparatory Examples 1B–1E.

TABLE 15

| Example | Resin (g) | Treated Colloidal Silica (OX-50) of Preparatory Example 2B (g) | Batch of Treated Fluoroalumino-silicate Glass | Treated Fluoroalumino-silicate Glass (g) |
|---|---|---|---|---|
| 9A | 47.17 | 4.95 | Preparatory Example 1B | 293.32 |
| 9B | 47.17 | 4.95 | Preparatory Example 1C | 223.32 |
| 9C | 38.56 | 4.05 | Preparatory Example 1B | 239.81 |
| 9D | 47.17 | 4.95 | Preparatory Example 1D | 243.32 |
| 9E | 31.45 | 3.30 | Preparatory Example 1E | 236.12 |
| 9F | 37.73 | 3.96 | Preparatory Example 1B | 244.96 |

EXAMPLES 10A–10E

Five dental restorative filling materials were prepared with the photo-polymerizable dental resin of Examples 9A–9F and inorganic fillers per Table 16. The treated colloidal silica (OX-50) is of Preparatory Example 2B and the treated fluoroaluminosilicate glass is of Preparatory Example 1A.

TABLE 16

| Example | Resin of EXAMPLE 9 AF (g) | Treated Colloidal Silica (OX-50) of Preparatory Example 2B (g) | Treated Fluoroalumino-silicate Glass of Preparatory Example 1A (g) |
|---|---|---|---|
| 10A | 64.21 | 5.68 | 241.27 |
| 10B | 65.23 | 5.32 | 225.76 |
| 10C | 65.86 | 4.96 | 210.52 |
| 10D | 57.70 | 3.67 | 155.63 |
| 10E | 57.38 | 3.33 | 141.29 |

EXAMPLE 11

The yield stress of the materials described in Examples 8–10 as well as those of some commercially available materials were measured at 25° C. and are tabulated in Table 17. The values of yield stress provided are averages of three measurements. The yield stress was measured using a parallel plate controlled-stress rheometer. The plate diameter was 20 mm, the separation between the plates was 2 mm, and the plates were lined with PSA-backed sandpaper (9 μm abrasive particle size) to prevent the filling material from slipping at the plate surface. The yield stress was determined by slowly ramping the stress up from a stress of 1 Pa-s to a stress sufficient to obtain a shear rate of 0.1 $sec^{-1}$. This stress ramping took place over 1000 sec in 100 logarithmically-spaced stress steps. The yield point was defined as the point at which shear-thinning behavior began when the log (viscosity) was plotted against log(stress).

The materials listed in Table 17 were evaluated by a group of dentists for their handling characteristics at mouth temperature. The materials that were most preferred lacked stickiness to placement instruments, easily adapted to a cavity preparation, did not slump, were easily contoured and feathered, and overall were easy to use and required a relatively short period of time to place. The materials that were most preferred had a yield stress between about 3000 and 9000 Pa at 25° C.

TABLE 17

| Sample | Yield Stress at 25 C. (Pa) | Handling Evaluation at 34 C. |
|---|---|---|
| Example 8A | 3679 | No stickiness. Easily adapts to cavity. No slump. Contours easily. Fast to place. |
| Example 8B | 4943 | No stickiness. Easily adapts to cavity. No slump. Contours easily. Fast to place. |
| Example 8C | 2264 | Too fluid |
| Example 8D | 9788 | No stickiness. Easily adapts to cavity. No slump. Contours easily. A little too stiff. |
| Example 9A | 7536 | No stickiness. Easy to work with. Packable into cavity preparation. Can fill cavity easily. Feathers well. No slump. |
| Example 9B | 6319 | No slump. Can contour easily and holds shape. No stickiness. Feathers well. |
| Example 9C | 5051 | No slump. Packs nicely into cavity preparation. Feathers well. No stickiness. |
| Example 9D | 5630 | A little too dry. A little rough to feather. Uneven flow. No slump. No stickiness. Fills cavity okay. |
| Example 9E | 5759 | No stickiness. Easy to use to fill cavity. Good feathering capability. No slump. Contours easily and shape stays. |
| Example 9F | 6467 | Feathers well. No slump. No stickiness. Good for filling cavity. |
| Example 10A | 2305 | No stickiness. Easily fills cavity. No slump. Contours easily. A little too thin. |
| Example 10B | 1299 | Slightly sticky. No slump. Does not feather extremely well because of stickiness. Flows easily into cavity preparation. |
| Example 10C | 701 | Sticky. No slump. Does not feather well because of stickiness. Flows easily into cavity. |
| Example 10D | 231 | Sticky. Stringy. Flows easily into cavity. Too runny. No slump. Does not feather well because of stickiness. |
| Example 10E | 217 | Sticky. Slightly stringy. Flows easily into cavity. No slump. Does not feather well because of stickiness. |
| Glacier (Southern Dental Industries Limited, Austrailia) Lots B09105 & B05115 | 1503 | Too thick. Did not feather well. Dry. Crumbly. No slump. Adapts to margins good. |
| Dyract (Dentsply International, Inc., Milford, DE) Lot C9406247 | 4328 | Does not flow well into cavity. Not packable. Sticky. Does not feather well because of stickiness. Slumps a very small amount. |
| Silux Plus (3M, St. Paul, MN) Lot 5702XL | 1711 | Flows well into cavity. A little sticky. Slight, but minimal slump. Feathers fine. |
| Aelite Flo (Bisco, Inc., Itasca, IL) Lots 059166, 039268, & 059180 | 108 | Sticky. Stringy. Flows very well into cavity. Does not feather well because of stickiness. Slumps. |
| Z100 (3M) Lot 19960325 | 692 | Feathers well. Slumps at margins. Flows fine into cavity. A small amount of stickiness. |
| TPH (Dentsply International, Inc.) Lot 9605061 | 5083 | Very sticky. Slumps slightly. Feathers okay, but stickiness complicates. Too thick to flow well into cavity. |
| Heliomolar (Vivadent Ets.) Lot 812056 | 5400 | Slightly sticky. Flows fine into cavity. No slump. Feathers okay. |

EXAMPLE 12

The yield stress of the materials described in Example 9 as well as those of some commercially available materials were measured at mouth temperature (34° C.) and are tabulated in Table 18. The measurement technique used is that described in Example 11. The values of yield stress provided are averages of two measurements. The materials listed in Table 18 were evaluated by a group of dentists for their handling characteristics at mouth temperature. The materials that were most preferred lacked stickiness to placement instruments, easily adapted to a cavity preparation, did not slump, were easily contoured and feathered, and overall were easy to use and required a relatively short period of time to place. The materials that were most preferred had a yield stress between about 2500 and 5000 Pa at 34° C.

TABLE 18

| Sample | Yield Stress at 34 C. (Pa) | Handling Evaluation at 34 C. |
|---|---|---|
| Example 9A | 4802 | No stickiness. Easy to work with. Packable into cavity preparation. Can fill cavity easily. Feathers well. No slump. |
| Example 9B | 4501 | No slump. Can contour easily and holds shape. No stickiness. Feathers well. |
| Example 9C | 3502 | No slump. Packs nicely into cavity preparation. Feathers well. No stickiness. |
| Example 9D | 2902 | A little too dry. A little rough to feather. Uneven flow. No slump. No stickiness. Fills cavity okay. |
| Example 9E | 3938 | No stickiness. Easy to use to fill cavity. Good feathering capability. No slump. Contours easily and shape stays. |

TABLE 18-continued

| Sample | Yield Stress at 34 C. (Pa) | Handling Evaluation at 34 C. |
|---|---|---|
| Example 9F | 4038 | Feathers well. No slump. No stickiness. Good for filling cavity. |
| Dyract Lot 9602180 | 3189 | Does not flow well into cavity. Not packable. Sticky. Does not feather well because of stickiness. Slumps a very small amount. |

EXAMPLE 13

The dynamic rheological properties of the materials described in Examples 8–10 as well as those of some commercially available materials were measured at 21° C. and are tabulated in Table 19. Measurements were made using a controlled-strain parallel plate rheometer. The plate diameter was 25 mm and the separation between the plates was 2 mm. Measurements were made at a strain in the linear viscoelastic region or at 0.1% strain, which ever was greater. The values of tan δ provided are averages of two measurements.

The materials listed in Table 19 were evaluated by a group of dentists for their handling characteristics at mouth temperature. The materials that were most preferred lacked stickiness to placement instruments, easily adapted to a cavity preparation, did not slump, were easily contoured and feathered, and overall were easy to use and required a relatively short period of time to place. The materials that were most preferred had a tan δ between about 1 and 1.7 at a frequency of 0.1 rad/sec; and between about 1 and 5 at 10 rad/sec.

TABLE 19

| Sample | tan δ at 0.1 rad/sec and 21 C. | tan δ at 10 rad/sec and 21 C. | Handling Evaluation at 34 C. |
|---|---|---|---|
| Example 8A | 1.248 | 1.862 | No stickiness. Easily adaps to cavity. No slump. Contours easily. Fast to place. |
| Example 8B | 1.131 | 1.010 | No stickiness. Easily adaps to cavity. No slump. Contours easily. Fast to place. |
| Example 8D | 1.650 | 1.808 | No stickiness. Easily adaps to cavity. No slump. Contours easily. A little too stiff. |
| Example 9A | 1.277 | 1.699 | No stickiness. Easy to work with. Packable into cavity preparation. Can fill cavity easily. Feathers well. No slump. |
| Example 9B | 1.368 | 1.703 | No slump. Can contour easily and holds shape. No stickiness. Feathers well. |
| Example 9C | 1.391 | 1.768 | No slump. Packs nicely into cavity preparation. Feathers well. No stickiness. |
| Example 9D | 0.868 | 1.211 | A little too dry. A little rough to feather. Uneven flow. No slump. No stickiness. Fills cavity okay. |
| Example 9E | 1.697 | 3.287 | No stickiness. Easy to use to fill cavity. Good feathering capability. No slump. Contours easily and shape stays. |
| Example 9F | 1.343 | 1.681 | Feathers well. No slump. No stickiness. Good for filling cavity. |
| Example 10A | 2.356 | 10.069 | No stickiness. Easily fills cavity. No slump. Contours easily. A little too thin. |
| Example 10B | 3.537 | 14.461 | Slightly sticky. No slump. Does not feather extremely well because of stickiness. Flows easily into cavity preparation. |
| Example 10C | 2.789 | 47.365 | Sticky. No slump. Does not feather well because of stickiness. Flows easily into cavity. |
| Example 10D | 11.534 | 20.815 | Sticky. Stringy. Flows easily into cavity. Too runny. No slump. Does not feather well because of stickiness. |
| Example 10E | 10.463 | 22.775 | Sticky. Slightly string. Flows easily into cavity. No slump. Does not feather well because of stickiness. |
| Dyract Lot C9406247 | 2.098 | 1.924 | Does not flow well into cavity. Not packable. Sticky. Does not feather well because of stickiness. Slumps a very small amount. |
| Silux Plus Lot 5702XL | 0.628 | 0.628 | Flows well into cavity. A little sticky. Slight, but minimal slump. Feathers fine. |
| Aelite Flo Lots 059166 & 039268 | 0.593 | 0.316 | Sticky. Stringy. Flows very well into cavity. Does not feather well because of stickiness. Slumps. |
| Z100- Lot 19960325 | 0.635 | 0.600 | Feathers well. Slumps at margins. Flows fine into cavity. A small amount of stickiness. |
| TPH Lot 9605061 | 0.727 | 0.338 | Very sticky. Slumps slightly. Feathers okay, but stickiness complicates. Too thick to flow well into cavity. |
| Heliomolar Lot 812056 | 1.036 | 0.940 | Slightly sticky. Flows fine into cavity. No slump. Feathers okay. |

EXAMPLE 14

The dynamic rheological properties of the materials described in Example 9 as well as those of some commercially available materials were measured at 34° C. and are tabulated in Table 20. The measurement techniques used are those described in Example 13. The values of tan δ provided are averages of two measurements. The materials listed in Table 20 were evaluated by a group of dentists for their handling characteristics at mouth temperature. The materials that were most preferred lacked stickiness to placement instruments, easily adapted to a cavity preparation, did not slump, were easily contoured and feathered, and overall were easy to use and required a relatively short period of time to place. The materials that were most preferred had a tan δ between about 0.4 and 1 at a frequency of 0.1 rad/sec; and between about 1 and 2.5 at 10 rad/sec.

TABLE 20

| Sample | tan delta at 0.1 rad/sec and 34 C. | tan delta at 10 rad/sec and 34 C. | Handling Evaluation at 34 C. |
|---|---|---|---|
| Example 9A | 0.905 | 1.257 | No stickiness. Easy to work with. Packable into cavity preparation. Can fill cavity easily. Feathers well. No slump. |
| Example 9B | 0.533 | 1.402 | No slump. Can contour easily and holds shape. No stickiness. Feathers well. |
| Example 9C | 0.916 | 1.791 | No slump. Packs nicely into cavity preparation. Feathers well. No stickiness. |
| Example 9D | 0.763 | 1.197 | A little too dry. A little rough to feather. Uneven flow. No slump. No stickiness. Fills cavity okay. |
| Example 9E | 1.044 | 2.435 | No stickiness. Easy to use to fill cavity. Good feathering capability. No slump. Contours easily and shape stays. |
| Example 9F | 0.936 | 1.690 | Feathers well. No slump. No stickiness. Good for filling cavity. |
| Dyract Lot 9602180 | 1.275 | 1.503 | Does not flow well into cavity. Not packable. Sticky. Does not feather well because of stickiness. Slumps a very small amount. |

EXAMPLE 15

The equilibrium steady shear viscosity of the materials in Example 9 and some commercially available filling materials was measured at 34° C. and at various shear rates. A controlled-stained rheometer was used with a 25 mm parallel plate geometry with the gap set to 2 mm. The plates were lined with 9 μm, PSA-backed sandpaper to prevent the filling materials from slipping at the plate surface at high shear rates. The results are summarized in Table 21. The values of viscosity provided for the Example 9 materials are averages of two to four measurements. The values of viscosity provided for the commercially available materials are single measurements. The dentist handling evaluations are reprinted in Table 21 for comparison. The materials that were most preferred lacked stickiness to placement instruments, easily adapted to a cavity preparation, did not slump, were easily contoured and feathered, and overall were easy to use and required a relatively short period of time to place. The materials that were most preferred had a viscosity at 0.001 sec$^{-1}$ between about 100,000 and 500,000 Pa-s at 34° C. The materials that were most preferred had a viscosity at 0.01 sec$^{-1}$ between about 80,000 and 250,000 Pa-s at 34° C. Lastly, the materials that were most preferred had a viscosity at 0.1 sec$^{-1}$ between about 20,000 and 100,000 Pa-s at 34° C.

TABLE 21

| Sample | Equilibrium Viscosity at 0.001/sec and 34 C. (Pa-s) | Equilibrium Viscosity at 0.01/sec and 34 C. (Pa-s) | Equilibrium Viscosity at 0.1/sec and 34 C. (Pa-s) | Handling Evaluations at 34 C. |
|---|---|---|---|---|
| Example 9A | 259,000 | 170,000 | 91,200 | No stickiness. Easy to work with. Packable into cavity preparation. Can fill cavity easily. Feathers well. No slump. |
| Example 9B | 105,500 | 88,050 | 71,900 | No slump. Can contour easily and holds shape. No stickiness. Feathers well. |
| Example 9C | 253,000 | 114,500 | | No slump. Packs nicely into cavity preparation. Feathers well. No stickiness. |
| Example 9D | 496,500 | 138,500 | | A little too dry. A little rough to feather. Uneven flow. No slump. No stickiness. Fills cavity okay. |
| Example 9E | 162,000 | 147,000 | | No stickiness. Easy to use to fill cavity. Good feathering capability. No slump. Contours easily and shape stays. |

TABLE 21-continued

| Sample | Equilibrium Viscosity at 0.001/sec and 34 C. (Pa-s) | Equilibrium Viscosity at 0.01/sec and 34 C. (Pa-s) | Equilibrium Viscosity at 0.1/sec and 34 C. (Pa-s) | Handling Evaluations at 34 C. |
|---|---|---|---|---|
| Example 9F | 374,750 | 196,000 | | Feathers well. No slump. No stickiness. Good for filling cavity. |
| Glacier Lot 60511 | 1,600,000 | 86,300 | 14,500 | Too thick. Did not feather well. Dry. Crumbly. No slump. Adapts to margins good. |
| Dyract Lot 9602180 | 274,000 | 99,400 | 54,500 | Does not flow well into cavity. Not packable. Sticky. Does not feather well because of stickiness. Slumps a very small amount. |
| Silux Plus Lot 19960708 | 396,000 | 57,900 | 7,870 | Flows well into cavity. A little sticky. Slight, but minimal slump. Feathers fine. |
| Aelite Flo Lots 059166 & 059116 | 77,700 | 12,600 | 1,530 | Sticky. Stringy. Flows very well into cavity. Does not feather well because of stickiness. Slumps. |
| Z100 Lot 19960325 | 921,000 | 76,500 | | Feathers well. Slumps at margins. Flows fine into cavity. A small amount of stickiness. |
| TPH Lot 9605061 | 295,000 | 30,700 | 2,980 | Very sticky. Slumps slightly. Feathers okay, but stickness complicates. Too thick to flow well into cavity. |
| Heliomolar Lot 812056 | 2,950,000 | 23,600 | 1,770 | Slightly sticky. Flows fine into cavity. No slump. Feathers okay. |

From the above examples it is apparent that only those pastes that had a yield stress between about 3000 and 9000 Pa at 25° C., a yield stress between about 2900 and 5000 Pa at 34° C., a viscosity at a shear rate of 0.001 sec−1 between about 100,000 and 500,000 Pa-s at 34° C., a viscosity at a shear rate of 0.01 sec−1 between about 80,000 and 250,000 Pa-s at 34° C., a viscosity at a shear rate of 0.1 sec−1 between about 20,000 and 100,000 Pa-s at 34° C., a tan δ value of between about 0.4 and 1 at 0.10 rad/s and 34° C., a tan δ value between about 1 and 2.5 at 10 rad/sec and 34° C., a tan δ value between about 1 and 1.7 at 0.10 rad/sec and 21° C., and a tan δ value between about 1 and 5 at 10 rad/sec and 21° C. were deemed by the dental practitioners to provide excellent handling properties while pastes that did not have all these properties were not preferred.

EXAMPLE 16 and COMPARATIVE EXAMPLES 1–3

The following comparative examples illustrate that each of the three following components of the dental compositions of the present invention, (1) a hydrophilic component, (2) an acid reactive filler, and (3) an acidic component, is necessary to provide the exceptionally good handling properties. In these examples, restorative filling materials were made by systematically omitting one of these three components and characterizing the handling. The filling materials prepared for these comparative examples are described in Table 22 below.

Example 16 in Table 22 is the control restorative filling material that contains all of the three foregoing components of the present invention. Comparative Example 1 is the same as Example 16 except that it lacks the hydrophilic component PNVP. Comparative Example 2 contains the non-acid reactive treated quartz of Preparatory Example 4 instead of the acid reactive treated fluoroaliminosilicate glass of Preparatory Example 1A. The treated quartz filler and treated fluoroaliminosilicate glass where of comparable particle sizes. Comparative Example 2 with the non-acid reactive treated quartz filler and Example 16 with the acid reactive fluoroaliminosilicate glass had the same volume percent inorganic filler which is necessary for making handling or rheological comparisons when the filler densities are different. Finally, Comparative Example 3 contains a non-acidic resin instead of the acidic resin in Example 16. For Comparative Example 3, BisGMA and TEGDMA were blended at a ratio such that the resin viscosity was comparable to that of the Example 16 resin. The viscosity of the Example 16 resin was approximately 5 Pa-s. The Comparative Example 3 resin contained 90/10 BisGMA/TEGDMA which gave a resin viscosity of approximately 5 Pa-s. This resin did not contain PNVP since the former was not hydrophilic enough to dissolve PNVP in appreciable quantities.

TABLE 22

| | | Example 16 | Comparative Example 1 | Comparative Example 2 | Comparative Example 3 |
|---|---|---|---|---|---|
| Resin | BisGMA | | | | 88.2490% |
| Weight | TEGDMA | | | | 9.8054% |
| Percents | GDMA | 28.6972% | 30.0154% | 28.6972% | |
| | CDMA/GDMA 50/50 | 65.0507% | 68.0390% | 65.0507% | |

TABLE 22-continued

|  |  | Example 16 | Comparative Example 1 | Comparative Example 2 | Comparative Example 3 |
|---|---|---|---|---|---|
|  | Tinuvin-P | 0.6247% | 0.6247% | 0.6247% | 0.6247% |
|  | BHT | 0.0925% | 0.0925% | 0.0925% | 0.0925% |
|  | CPQ | 0.2460% | 0.2460% | 0.2460% | 0.2460% |
|  | EDMAB | 0.9824% | 0.9824% | 0.9824% | 0.9824% |
|  | PNVP | 4.3065% | 0.0000% | 4.3065% | 0.0000% |
|  | Total | 100.0000% | 100.0000% | 100.0000% | 100.0000% |
| Paste | BisGMA | 0.0000% | 0.0000% | 0.0000% | 15.6024% |
| Weight | TEGDMA | 0.0000% | 0.0000% | 0.0000% | 1.7336% |
| Percents | GDMA | 5.0737% | 5.3067% | 9.1948% | 0.0000% |
|  | CDMA/GDMA 50/50 | 11.5010% | 12.0293% | 20.8427% | 0.0000% |
|  | Tinuvin-P | 0.1104% | 0.1104% | 0.2002% | 0.1104% |
|  | BHT | 0.0164% | 0.0164% | 0.0296% | 0.0164% |
|  | CPQ | 0.0435% | 0.0435% | 0.0788% | 0.0435% |
|  | EDMAB | 0.1737% | 0.1737% | 0.3148% | 0.1737% |
|  | PNVP | 0.7614% | 0.0000% | 1.3798% | 0.0000% |
|  | Treated Colloidal Silica (OX-50) of Preparatory Example 2B | 1.9000% | 1.9000% | 1.9000% | 1.9000% |
|  | Treated Fluoralimino-silica Glass of Preparatory Example 1A | 80.4200% | 80.4200% | 0.0000% | 80.4200% |
|  | Treated Quartz Filler of Preparatory Example 4 | 0.0000% | 0.0000% | 66.0593% | 0.0000% |
|  | Total | 100.0000% | 100.0000% | 100.0000% | 100.0000% |

The equilibrium viscosities of the filling materials described in Table 22 were measured as a function of shear rate at 34° C. using the method described in Example 15. This data is tabulated in Table 23. The viscosity values provided represent single measurements. The data show that when any one of the three foregoing components is omitted from the filling material, the viscosity is very different from that of the filling material of the present invention (Example 16). We can conclude, then, that it is the synergy between the hydrophilic component, the acid reactive filler, and the acidic component that is responsible for the exceptionally good handling properties of the present invention.

The filling materials described in Table 22 were evaluated by a group of dentists for their handling characteristics at mouth temperature (34° C.). Their comments are summarized in Table 23. Example 16 was most preferred because it lacked stickiness to placement instruments, easily adapted to a cavity preparation, did not slump, was easily contoured and feathered, and overall was easy to use and required a relatively short period of time to place. Only Example 16 in Table 23 had a viscosity at 0.001 sec$^{-1}$ between about 100,000 and 500,000 Pa-s at 34° C. Only Example 16 had a viscosity at 0.01 sec$^{-1}$ between about 80,000 and 250,000 Pa-s at 34° C. Only Example 16 had a viscosity at 0.1 sec$^{-1}$ between about 20,000 and 100,000 Pa-s at 34° C. Comparative Examples 1–3 did not satisfy these viscosity criteria for good handling properties.

TABLE 23

| Sample | Equilibrium Viscosity at 0.001/sec and 34 C. (Pa-s) | Equilibrium Viscosity at 0.01/sec and 34 C. (Pa-s) | Equilibrium Viscosity at 0.1/sec and 34 C. (Pa-s) | Handling Evaluation at 34 C. |
|---|---|---|---|---|
| Example 16 | 396,050 | 120,670 | 32,480 | No stickiness. No slump. Can contour easily and holds shape. Feathers well. Packs nicely into cavity preparation. |
| Comparative Example 1 | 59,395 | 17,405 | 7,068 | Too runny. Slumps. Difficult to contour. |
| Comparative Example 2 | 40,191 | 5,493 | 1,076 | Very sticky. Too runny. Slumps badly. Difficult to contour. |
| Comparative Example 3 | 32,016,000 | 2,397,700 |  | Too stiff. No slump. Doesn't fill cavity easily. Difficult to feather. |

The dynamic rheological properties of the materials described in Table 21 were measured at 34° C. and are tabulated in Table 24. The measurement techniques used are those described in Example 13. The tan δ values provided represent single measurements. The dentist handling evaluations are reprinted in Table 24 for comparison. Example 16 was most preferred because it lacked stickiness to placement instruments, easily adapted to a cavity preparation, did not slump, was easily contoured and feathered, and overall was easy to use and required a relatively short period of time to place. Only Example 16 in Table 24 had a tan δ between about 0.4 and 1 at a frequency of 0.1 rad/sec; and between about 1 and 2.5 at 10 rad/sec. Comparative Examples 1–3 did not satisfy this tan δ criteria for good handling properties.

TABLE 24

| | tan delta at 0.1 rad/sec and 34 C. | tan delta at 10 rad/sec and 34 C. | Handling Evaluation at 34 C. |
|---|---|---|---|
| Example 16 | 0.653 | 1.224 | No stickiness. No slump. Can contour easily and holds shape. Feathers well. Packs nicely into cavity preparation. |
| Comparative Example 1 | 1.550 | 1.101 | Too runny. Slumps. Difficult to contour. |
| Comparative Example 2 | 0.720 | 0.714 | Very sticky. Too runny. Slumps badly. Difficult to contour. |
| Comparative Example 3 | 0.815 | 0.326 | Too stiff. No slump. Doesn't fill cavity easily. Difficult to feather. |

What is claimed:

1. A dental composition comprising
   a) a polymerizable component,
   b) a fluoride-releasing material,
   c) a hydrophilic component having a molecular weight greater than about 5,000,
   d) a polymerization initiator,
   e) an acidic component,
said dental composition being substantially free of added water, said composition having a Water Uptake Value of at least about 1.5 g of water per 100 g composition in 2 weeks.

2. A dental composition according to claim 1, wherein said polymerizable component and said hydrophilic component are provided as a single compound.

3. A dental composition according to claim 1, wherein said polymerizable component and said acidic component are provided as a single compound.

4. A dental composition according to claim 1, wherein said hydrophilic component and said acidic component are provided as a single compound.

5. A dental composition according to claim 1, wherein said polymerizable component is a free radically polymerizable material.

6. A dental composition according to claim 1, wherein said polymerizable component has a molecular weight of between about 100 to 5000.

7. A dental composition according to claim 1, wherein said fluoride releasing material comprises a metal complex described by formula $$M(G)_g(F)_n \text{ or } M(G)_g(ZF_m)_n$$

where M represents an element capable of forming a cationic species and having a valency of 2 or more,
   G is an organic chelating moiety capable of complexing with the element M
   Z is hydrogen, boron, nitrogen, phosphorus, sulfur, antimony, arsenic
   F is a fluoride atom
   g, m and n are at least 1.

8. A dental composition according to claim 7, wherein M is selected from the group consisting of $Ca^{+2}$, $Mg^{+2}$, $SR^{+2}$, $Zn^{+2}$, $Al^{+1}$, $Zr^{+4}$, $Sn^{+2}$, $Yb^{+3}$, $Y^{+3}$, and $Sn^{+4}$.

9. A dental composition according to claim 7, wherein M is $Zn^{+2}$.

10. A dental composition according to claim 7, wherein said fluoride releasing material additionally comprises a fluoride-releasing fluoroaluminosilicate glass.

11. A dental composition according to claim 1, wherein said hydrophilic component contains acidic functionality and non-acidic hydrophilic functionality.

12. A dental composition according to claim 1, wherein said hydrophilic component contains no acidic functionalities.

13. A dental composition according to claim 1, wherein said hydrophilic component is selected from monomers or polymers comprising functionalities selected from the group consisting of pyrrolidone, sulfonate ($SO_3$), sulfonic ($SO_2$), N-oxysuccinimide, N-vinylacetamide and acrylamide functionalities.

14. A dental composition according to claim 1, wherein said hydrophilic component is selected from the group consisting of polyalkylene oxides, polyethers, polyethyleneimines, polyacrylamides, polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized forms, polyethyleneimine and its salts, polyethylene sulfonic acid and polyaryl sulfonic acids in unionized, partially neutralized or fully neutralized form, and polyphoshoric and phosphonic acids in unionized, partially neutralized or fully neutralized form.

15. A dental composition according to claim 1, wherein said hydrophilic component is selected from the group consisting of polyoxymethylene, polyethyleneoxide, polypropylene oxide and polyvinylmethyl ether.

16. A dental composition according to claim 1, wherein said acidic component is selected from the group consisting of monomers, oligomers, or polymers of molecular weight less than 10,000 and containing at least one acidic group selected from oxyacids or thio-oxy acids of B, C, N, S, and P.

17. A dental composition according to claim 16, wherein said acidic component is a compound that is an acid of C or P.

18. A dental composition according to claim 1, said composition comprising
   a) a polymerizable component containing acid functionality defined by the structure $(P)_p$—$(Q)_q$—$(R)_r$—
      where P=backbone with acidic functionality
      Q=backbone with a polymerizable functionality,
      R=backbone of a non-reactive modifying unit
      $p \geq 1$, $q > 1$, and $r = 0$ or more;
   b) a fluoride-releasing material,
   c) a hydrophilic component,
   d) a polymerization initiator,
said dental composition being substantially free of added water, said composition having a Water Uptake Value of at least about 1.5 g of water per 100 g composition in 2 weeks.

19. A dental composition according to claim 18, wherein said polymerizable component containing acid functionality is selected from the group consisting of acryloyl or methacryloyl substituted polycarboxylic acids, phosphoric acid esters of hydroxyethyl methacrylate, phosphoric acid esters of hydroxy propyl methacrylate, acrylates and methacrylates of pentaerythritol dimethacrylate.

20. A dental composition according to claim 1, additionally comprising a reactive filler.

21. A dental composition according to claim 1, additionally comprising a non-reactive filler.

22. A dental composition comprising
a) a polymerizable component,
b) acid reactive filler,
c) a hydrophilic component having a molecular weight greater than about 5,000,
d) a polymerization initiator, and
e) an acidic component;
the above materials being provided in amounts sufficient that the resulting composition has the following rheological properties:
1) a yield stress between about 3000 and 9000 Pa at 25° C., and between about 29000 and 5000 Pa at 34° C.,
2) a viscosity of between about 100,000 and 500,000 Pa-s at 34° C. and shear rate of 0.001 sec–1, a viscosity of between about 80,000 and 250,000 Pa-s at 34° C. at a shear rate of 0.01 sec–1, and between about 20,000 and 100,000 Pa-s at 34° C. at a shear rate of 0.1 sec–1, and
3) a tan δ value of between about 0.4 and 1 at 0.10 rad/s and 34° C., a tan δ value between about 1 and 2.5 at 34° C. and 10 rad/sec, a tan δ value between about 1 and 1.7 at 21° C. and 0.10 rad/sec, and a tan δ value between about 1 and 5 at 21° C. and 10 rad/sec.

23. A dental composition according to claim 22, which composition is substantially free of added water.

24. A dental composition according to claim 22, wherein the polymerizable component has a molecular weight of between about 100 to 5000.

25. A dental composition according to claim 22, wherein the polymerizable component has a molecular weight between about 300 and 1000.

26. A dental composition according to claim 22, wherein the polymerizable component has a viscosity of less than about 2 Pa-s.

27. A dental composition according to claim 22, wherein the polymerizable component has a viscosity of less than about 0.5 Pa-s.

28. A dental composition according to claim 22, wherein the polymerizable component has a viscosity of less than about 0.3 Pa-s.

29. A dental composition according to claim 22, wherein the polymerizable component is selected from the group consisting of esters of acrylic or methacrylic acid.

30. A dental composition according to claim 22, wherein the polymerizable component is selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate, hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A, glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-b 1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxyphenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, and mixtures thereof.

31. A dental composition according to claim 22, wherein the hydrophilic component has a molecular weight between about 5,000 and 500,000.

32. A dental composition according to claim 22, wherein the hydrophilic component has a molecular weight between about 5,000 and 100,000.

33. A dental composition according to claim 22, wherein the hydrophilic component is poly-N-vinylpyrrolidone.

34. A dental composition according to claim 22, wherein the acid reactive filler is a filler that releases fluoride.

35. A dental composition according to claim 22, wherein the acid reactive filler is a fluoroaluminosilicate glass.

36. A dental composition according to claim 22, which additionally comprises a non-acid reactive filler.

37. A dental composition according to claim 36, wherein the non-acid reactive filler has a maximum particle diameter less than about 10 micrometers and an average particle diameter less than about 1.0 micrometers.

38. A dental composition according to claim 36, wherein the non-acid reactive filler has a maximum particle diameter less than about 1.0 micrometers and an average particle size of diameter less than about 0.1 micrometer.

39. A dental composition according to claim 36, wherein the non-acid reactive filler is a colloidal silica.

40. A dental composition according to claim 22, wherein at least a portion of the polymerizable component and at least a portion of the acidic component of the composition are provided by the same chemical compound.

41. A dental composition according to claim 22, wherein the polymerizable component is a compound having the structure $(P)_p\text{---}(Q)_q\text{---}(R)_r$
where P=backbone with acidic functionality
 Q=backbone with an acrylate or methacrylate curable group,
 R=backbone of a non-reactive modifying unit
 $p \geq 1$, $q>1$, and $r=0$ or more.

42. A dental composition according to claim 41, wherein the curable group is linked to the backbone through an amide linkage.

43. A dental composition according to claim 41, wherein the polymerizable component has a molecular weight of between about 300–5000.

44. A dental composition according to claim 22, which comprises glycerol dimethacrylate, polymerization initiators, colloidal silica, fluoroaluminosilicate glass, and a compound of molecular weight of between about 300–5000 having the structure $(P)_p\text{---}(Q)_q\text{---}(R)_r$
where P=backbone with acidic functionality
 Q=backbone with an acrylate or methacrylate curable group,
 R=backbone of a non-reactive modifying unit
 $p \geq 1$, $q>1$, and $r=0$ or more,
 wherein the curable group is linked to the backbone through an amide linkage.

45. A dental composition according to claim 1, wherein the hydrophilic component has a molecular weight between about 5,000 and 500,000.

46. A dental composition according to claim 45, wherein the hydrophilic component has a molecular weight between about 5,000 and 100,000.

47. A dental composition comprising
 a) a polymerizable component,
 b) a fluoride-releasing material,
 c) an oligomeric or polymeric hydrophilic component,
 d) a polymerization initiator,
 e) an acidic component,
said dental composition being substantially free of added water, said composition having a Water Uptake Value of at least about 1.5 g of water per 100 g composition in 2 weeks.

* * * * *

UNITED STATES PATENT AND TRADEMARK OFFICE
CERTIFICATE OF CORRECTION

PATENT NO. : 6,126,922
DATED : October 3, 2000
INVENTOR(S) : Rozzi, Sharon M.

It is certified that error appears in the above-identified patent and that said Letters Patent is hereby corrected as shown below:

Title page,
Item [56], References Cited, U.S. PATENT DOCUMENTS, please add:

| | | |
|---|---|---|
| -- 3,018,262 | 1/1963 | Schroeder |
| 3,117,099 | 1/1964 | Proops |
| 3,655,605 | 4/1972 | Smith |
| 3,721,644 | 3/1973 | Stoffey |
| 3,766,132 | 10/1973 | Lee |
| 3,770,811 | 11/1973 | Lee |
| 3,814,717 | 6/1974 | Wilson |
| 4,143,018 | 3/1979 | Crisp |
| 4,150,485 | 4/1979 | Lee |
| 4,209,434 | 6/1980 | Wilson |
| 4,360,605 | 11/1982 | Schmitt |
| 4,376,835 | 3/1983 | Schmitt |
| 4,503,169 | 3/1985 | Randklev |
| 4,514,174 | 4/1985 | Dougherty |
| 4,695,251 | 9/1987 | Randklev |
| 5,151,453 | 9/1992 | Ibsen |
| 5,154,762 | 10/1992 | Mitra |
| 5,318,999 | 6/1994 | Mitra |
| 5,332,429 | 7/1994 | Mitra -- |

FOREIGN PATENT DOCUMENTS, please add:

| | | |
|---|---|---|
| -- 4447275 | 7/1996 | Germany |
| 176777 | | EPO |
| 436382 | | EPO |
| 56120610 | 9/1981 | Japan |
| 03077804 | 4/1991 | Japan |
| 06065022 | 3/1994 | Japan |
| 07061904 | 3/1995 | Japan |
| 08119820 | 5/1996 | Japan -- |

OTHER PUBLICATIONS, please add:
-- Lee, H.L. et al. (Aust. Dent. J., 22(4), 1977, 232-5).
Rheology Principles, Measurements and Applications, C.W. Macosko, VCH Publishers, Inc., New York 1994, p. 92. --

UNITED STATES PATENT AND TRADEMARK OFFICE
CERTIFICATE OF CORRECTION

PATENT NO.    : 6,126,922
DATED         : October 3, 2000
INVENTOR(S)   : Rozzi, Sharon M.

It is certified that error appears in the above-identified patent and that said Letters Patent is hereby corrected as shown below:

<u>Column 5,</u>
Line 56, delete "di-1-" and insert in place thereof -- di b 1- --.

<u>Column 23,</u>
Line 13, delete "350ºC." and insert in place thereof -- 35º --.

Signed and Sealed this

Thirteenth Day of May, 2003

JAMES E. ROGAN
*Director of the United States Patent and Trademark Office*